US010760103B2

(12) United States Patent
Bowie et al.

(10) Patent No.: US 10,760,103 B2
(45) Date of Patent: Sep. 1, 2020

(54) MOLECULAR RHEOSTAT FOR COFACTOR BALANCE

(71) Applicant: The Regents of the University of California, Oakland, CA (US)

(72) Inventors: James U. Bowie, Los Angeles, CA (US); Tyler P. Korman, Sierra Madre, CA (US); Paul H. Opgenorth, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/342,849

(22) PCT Filed: Oct. 18, 2017

(86) PCT No.: PCT/US2017/057156
§ 371 (c)(1),
(2) Date: Apr. 17, 2019

(87) PCT Pub. No.: WO2018/075624
PCT Pub. Date: Apr. 26, 2018

(65) Prior Publication Data
US 2019/0264239 A1    Aug. 29, 2019

Related U.S. Application Data

(60) Provisional application No. 62/409,731, filed on Oct. 18, 2016.

(51) Int. Cl.
| | |
|---|---|
| C12P 7/16 | (2006.01) |
| C12N 9/02 | (2006.01) |
| C12N 9/12 | (2006.01) |
| C12P 13/06 | (2006.01) |
| C12P 13/08 | (2006.01) |

(52) U.S. Cl.
CPC .............. *C12P 7/16* (2013.01); *C12N 9/0008* (2013.01); *C12N 9/1217* (2013.01); *C12P 13/06* (2013.01); *C12P 13/08* (2013.01); *C12Y 102/01012* (2013.01); *C12Y 207/02003* (2013.01); *Y02E 50/10* (2013.01)

(58) Field of Classification Search
CPC .................................... C12P 7/16; C12N 9/08
See application file for complete search history.

(56) References Cited

U.S. PATENT DOCUMENTS

2006/0075522 A1    4/2006 Abad et al.

FOREIGN PATENT DOCUMENTS

| WO | 2015/153929 A2 | 10/2015 |
|---|---|---|
| WO | 2017/015429 A2 | 1/2017 |

OTHER PUBLICATIONS

Mohri, Mineko, International Preliminary Report on Patentability and Written Opinion, The International Bureau of WIPO, dated May 2, 2019.
Fillinger et al., "Two Glyceraldeyhyde-3-phosphate Dehydrogenases with Opposite Physiological Roles in a Nonphotosynthetic Bacterium", J. Biol. Chem., May 12, 2000, vol. 275, No. 19, pp. 14031-14037.
Iancu, "Cell-Free Biofuel Production using an In Vitro Synthetic Biochemistry Platform and Quantification of Isobutanol Tolerance of Synthesis Enzymes", University of California, Los Angeles Thesis published Jan. 1, 2016, 70 pages, Available on the internet: < https://cloudfront.escholarship.org/dist/prd/content/qt3nt366qc/qt3nt366qc.pdf>.
UniProtKB P18912.PGC_Geose. Aug. 1, 1992 [retrieved Feb. 20, 2018]. Available on the internet: <https://www.uniprot/P18912>.
Young, Lee W., International Search Report and Written Opinion, United States Patent and Trademark Office, PCT/US17/57156, dated Mar. 8, 2018.
Centeno-Leija, Sara et al., "Improving poly-3-hydroxybutyrate production in *Escherichia coli* by combining the ncrease in the NADPH pool and acetyl-CoA availability", Antonie Van Leeuwenhoek, vol. 105, No. 4, Feb. 6, 2014, pp. 687-696.
Jiang et al, "Metabolic engineering of Corynebacterium glutamicumfor increasing the production ofl-omithine by increasing NADPH availability", Journal of Industrial Microbiology and Biotechnology, Basingstoke, GB, vol. 40, No. 10, Jul. 9, 2013, pp. 1143-1151.
Maceachran, Daniel P. et al., "The Rhodococcus opacus TadD protein mediates triacylglycerol metabolism by regulating intracellular NAD (P)H pools," Microbial Cell Factories, vol. 12, No. 1, 104, Nov. 9, 2013, pp. 1-12.
Schroder, Gunnar, Search Report, European Patent Office, Application No. 17862069.6, dated Jun. 12, 2020.
Takeno et al., "L-Lysine production independent of the oxidative pentose phosphate pathway by Corynebacterium glutamicum with the Streptococcus mutans gapN gene", Metabolic Engineering, vol. 37, Sep. 2016, pp. 1-10.

*Primary Examiner* — Karen Cochrane Carlson
(74) *Attorney, Agent, or Firm* — Gavrilovich, Dodd & Lindsey LLP

(57) ABSTRACT

The disclosure provides a metabolic pathway for producing a metabolite, the metabolic pathway having a co-factor regulatory system for cofactor utilization in the metabolic pathway.

21 Claims, 8 Drawing Sheets

Specification includes a Sequence Listing.

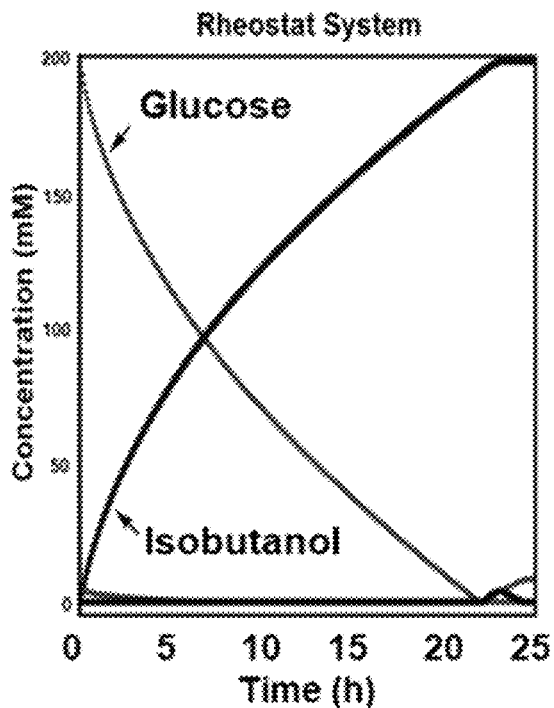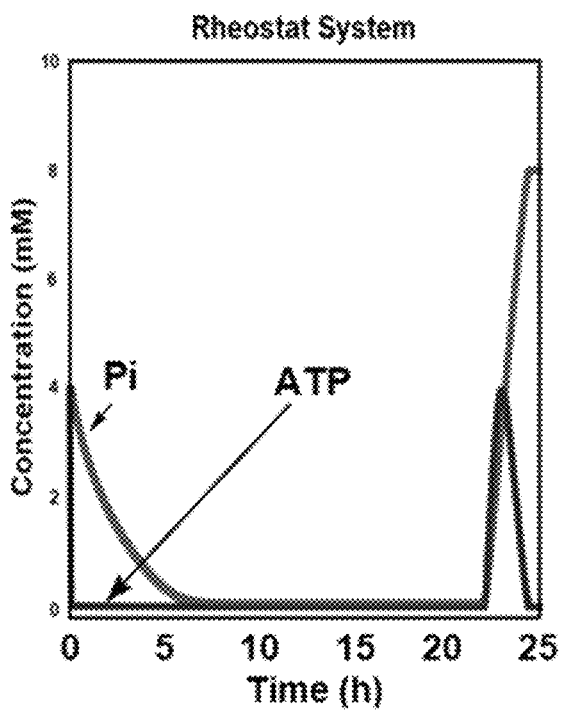
FIG. 4A
FIG. 4B
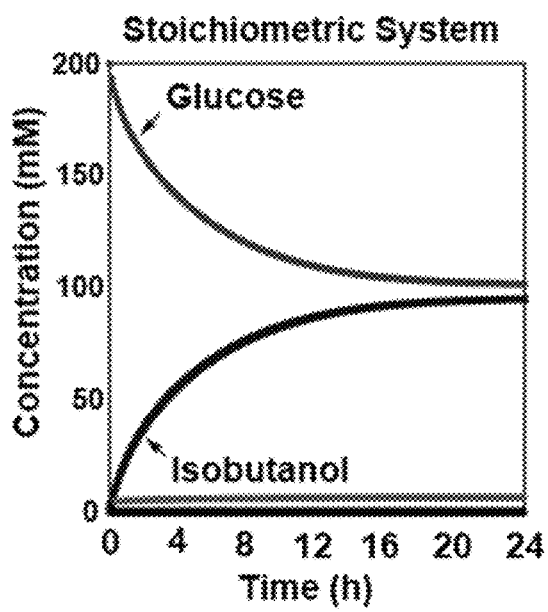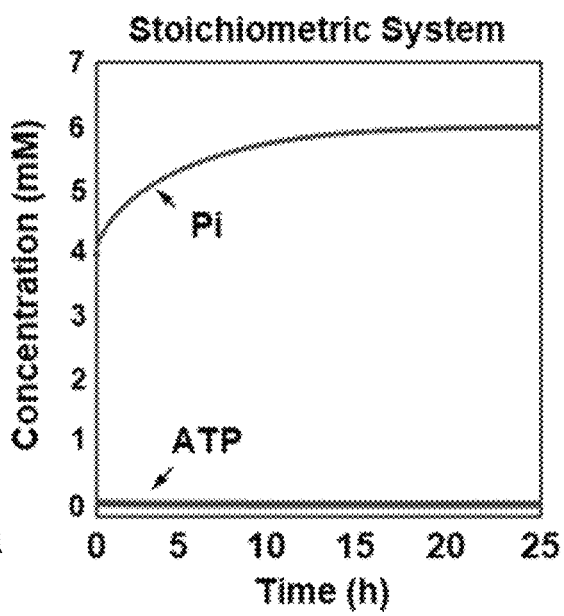
FIG. 4C
FIG. 4D

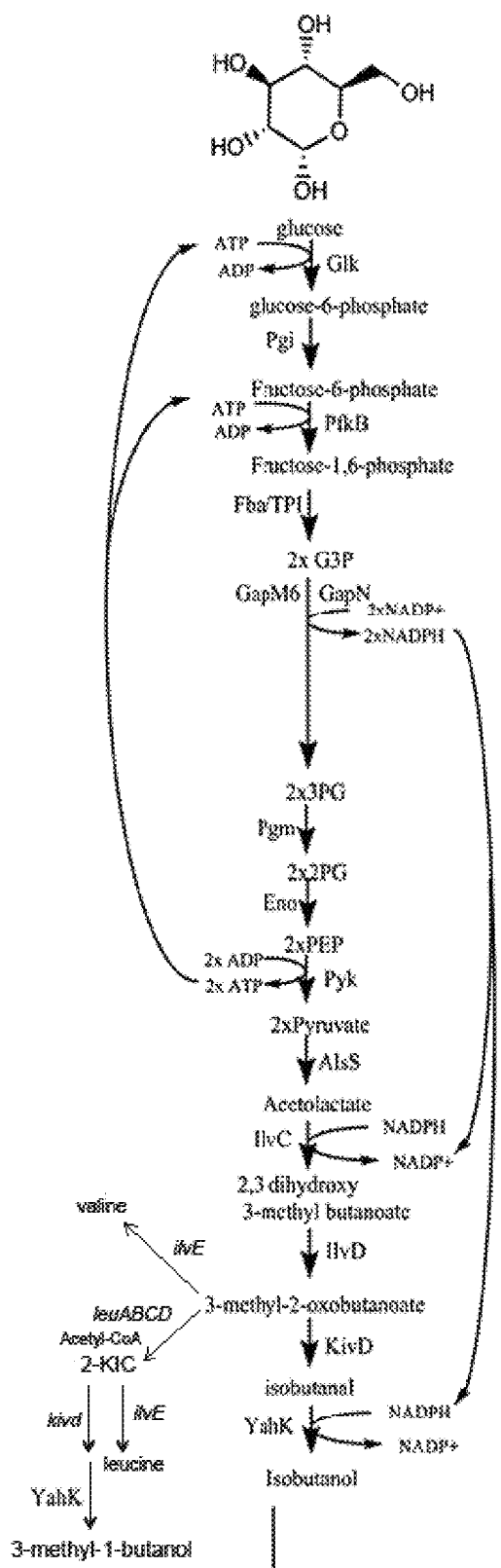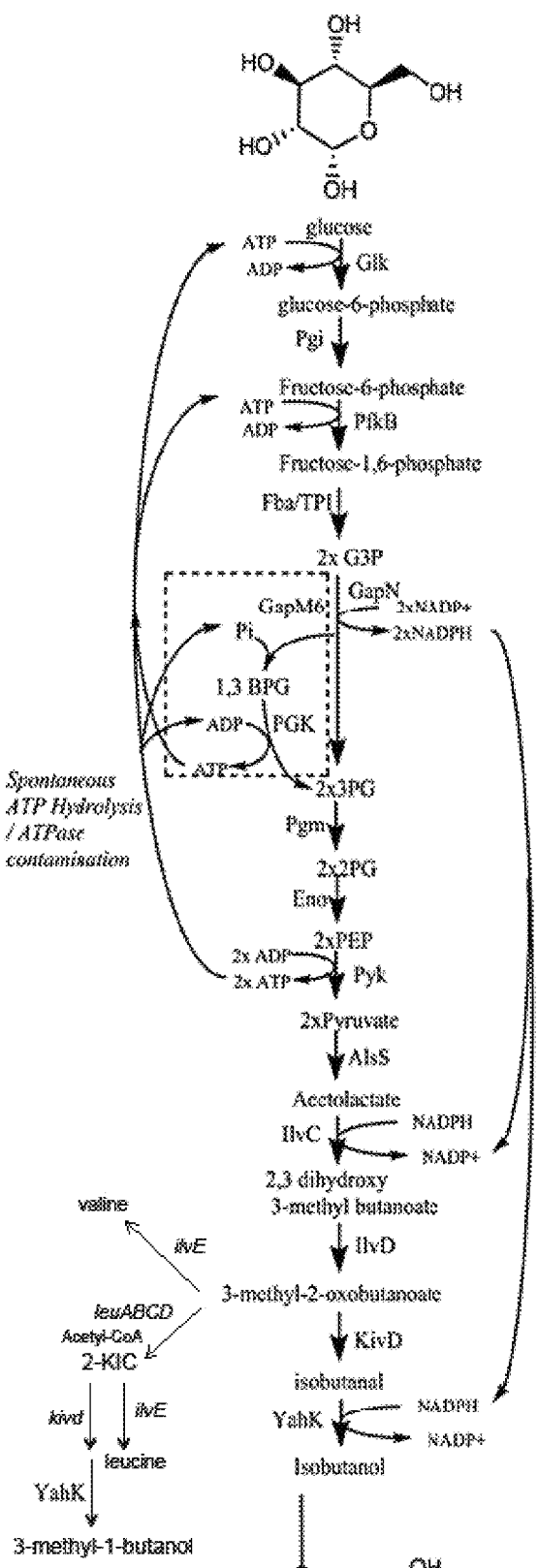
FIG. 6A
FIG. 6B

MOLECULAR RHEOSTAT FOR COFACTOR BALANCE

CROSS REFERENCE TO RELATED APPLICATIONS

This is a U.S. National Phase Application filed under 35 U.S.C. § 371 and claims priority to International Application No. PCT/US2017/057156, filed Oct. 18, 2017, which application claims priority to U.S. Provisional Application Ser. No. 62/409,731, filed Oct. 18, 2016, the disclosures of which are incorporated herein by reference.

STATEMENT REGARDING FEDERALLY SPONSORED RESEARCH

This invention was made with Government support under Grant No. DE-AR0000556, awarded by the Department of Energy. The Government has certain rights in the invention.

INCORPORATION BY REFERENCE OF SEQUENCE LISTING

Accompanying this filing is a Sequence Listing entitled "Sequence_ST25.txt", created on Oct. 18, 2017 and having 56,906 bytes of data, machine formatted on IBM-PC, MS-Windows operating system. The sequence listing is hereby incorporated by reference in its entirety for all purposes.

TECHNICAL FIELD

The disclosure provides engineered pathways for chemical production using a molecular rheostate for ATP balance.

BACKGROUND

Over the past decades there has been a keen interest in engineering cellular metabolism for the production of "green" chemicals that could ween us off of our reliance on petrochemicals. One method is to perform a desired biochemical conversions with purified enzymes or cell extracts. Cell free metabolic systems have many advantages over in vivo efforts such as continuous product production, ease of product removal, near 100% yields, and no cell toxicity issues.

Building cell free pathways that can economically sustain high flux for long periods of time without the metabolic regulatory systems that exist in cells requires new design principles, a field referred to as "synthetic biochemistry". A key consideration in synthetic biochemistry system design is the generation, regulation and recycling of high energy cofactors such as ATP, NADH and NADPH. Generally high energy cofactors are generated in a catabolic or breakdown phase (e.g. glycolysis), then utilized and regenerated in an anabolic or build phase where the desired chemicals are constructed. The simplest way to design synthetic biochemistry systems is to demand perfect stoichiometry, so that if two ATP are generated in the breakdown phase, then two ATP are utilized in the build phase. Stoichiometric systems can allow flux through the pathway for a period of time, but the second law of thermodynamics dictates that they will eventually wind down as ATP is hydrolyzed or NADH is oxidized by undesired side reactions.

SUMMARY

The disclosure provides a recombinant, artificial or engineered metabolic pathway comprising a plurality of enzymatic steps that converts a substrate to a product, wherein the pathway comprises a non-naturally occurring molecular rheostat system the alternates between or simultaneously uses a first cofactor pathway for the production of a metabolite and a second cofactor pathway for the production of the metabolite depending upon cofactor availability. In one embodiment, the pathway comprises: (a) a first enzymatic step that converts a first metabolite to a second metabolite using a first co-factor; (b) a second enzymatic step that converts the first metabolite to the second metabolite using a first co-factor and second co-factor or second co-factor; wherein the first enzymatic step is active when the second co-factor level is low and wherein the second enzymatic step is active when the second co-factor level is high. In another or further embodiment, the first cofactor is an oxidizing/reducing co-factors and the second cofactor is $P_i$. In still another embodiment of any of the foregoing embodiments, the oxidizing/reducing co-factors are $NAD^+/NADH$, $NADP^+/NADPH$ or $FAD^+/FADH$. In still another embodiment of any of the foregoing embodiments, the first cofactor comprises $NADP^+/NADPH$. In still another embodiment of any of the foregoing embodiments, the metabolic pathway comprises the conversion of glyceraldehyde-3-phosphate to 3-phosphoglycerate. In still another embodiment of any of the foregoing embodiments, the metabolic pathway produces a metabolite selected from the group consisting of isobutanol, 3-methyl-1-butanol, leucine, and valine. In still another embodiment of any of the foregoing embodiments, the pathway comprises the conversion of glyceraldehyde-3-phosphate to 1,3-bisphosphoglycerate and 1,3-bisphosphoglycerate to 3-phosphoglycerate. In still another embodiment of any of the foregoing embodiments, the pathway comprises (i) an enzyme that converts glyceraldehyde-3-phosphate (G3P) and $NADP^+$ to 3-phosphoglycerate (3PG) and NADPH; and (ii) an enzyme that converts glyceraldehyde-3-phosphate (G3P), $NADP^+$ and free phosphate (Pi) to 1,3-bisphosphoglycerate (1,3BPG) and (iii) an enzyme that converts 1,3 bisphosphoglycerate (1,3BPG) and ADP to 3-phophoglycerate and ATP. In still another embodiment of any of the foregoing embodiments, the enzyme of (i) comprises a NADP-dependent glyceraldehyde-3-phosphate dehydrogenase (GapN). In still another embodiment of any of the foregoing embodiments, the GapN is obtained from *S. mutans*. In still another embodiment of any of the foregoing embodiments, the enzyme of (ii) comprises a mutant glyceraldehyde-3-phosphate dehydrogenase (mGap) that comprises D34A/L35R/T36K mutations relative to SEQ ID NO:6. In still another embodiment of any of the foregoing embodiments, the enzyme of (ii) comprises a mutant glyceraldehyde-3-phosphate dehydrogenase (mGap) that has a sequence that is at least 95% identical to SEQ ID NO:6 and comprises D34A/L35R/T36K mutations. In still another embodiment of any of the foregoing embodiments, the enzyme of (iii) comprises enzyme commission number (EC number) EC 2.7.2.3. In still another embodiment of any of the foregoing embodiments, the enzyme of (iii) is a phosphoglycerate kinase. In still another embodiment of any of the foregoing embodiments, the phosphoglycerate kinase is a Pgk from *G. stearothermophilus*. In still another embodiment of any of the foregoing embodiments, the enzyme of (iii) has a sequence that is at least 95% identical to SEQ ID NO:7 and has phosphoglycerate kinase activity. In still another embodiment of any of the foregoing embodiments, the molecular rheostat comprise the enzymes of (i) a NADP-dependent glyceraldehyde-3-phosphate dehydrogenase (GapN), (ii) a mutant glyceraldenhyde-3-phosphate dehydrogenase that utilizes $NADP^+$ and (iii) a phosphoglycerate kinase. In still another embodiment of any of the foregoing embodiments, the pathway comprises (i) a polypeptide that catalyzes the production of glucose-6-phosphate (G6P) from glucose; (ii) a polypeptide that catalyzes the production of Fructose-6-phosphate (F6P) from glucose-6-phosphate (G6P); (iii) a polypeptide the catalyzes the conversion/phosphorylation of fructose-6-phosphate (F6P) to fructose-1,6-phosphate; (iv) a polypeptide that converts fructose-1,6-phosphate to two glyceraldehyde-3-phosphates (G3P); (v) a molecular rheostat comprising (a) an enzyme that converts glyceraldehyde-3-phosphate (G3P) and $NADP^+$ to 3-phosphoglycerate (3PG) and NADPH and (b) an enzyme that converts glyceraldehyde-3-phosphate (G3P), $NADP^+$ and free phosphate (Pi) to 1,3-bisphosphoglycerate (1,3BPG) and (c) an enzyme that converts 1,3 bisphosphglycerate (1,3BPG) and ADP to 3-phophoglycerate (3pG) and ATP; (vi) a polypeptide that converts 3-phosphoglycerate (3PG) to 2-phosphoglycerate (2PG); (vii) a polypeptide that converts 2-phosphoglycerate (2PG) to phosphoenolpyruvate (PEP); (viii) a polypeptide that converts phosphoenolpyruvate (PEP) to pyruvate; (ix) a polypeptide that converts pyruvate to acetolactate; (x) a polypeptide that converts acetolactate and NADPH to 2,3 dihydroxy-3-methyl butanoate and $NADP^+$; (xi) a polypeptide that converts 2,3 dihydroxy-3-methyl butanoate to 3-methyl-2-oxobutanoate; (xii) a polypeptide that converts 3-methyl-2-oxobutanoate to isobutanal and (xiii) a polypeptide that coverts isobutanal and NADPH to isobutanol and $NADP^+$. In still another embodiment of any of the foregoing embodiments, wherein the pathway is in a cell-free system. In still another embodiment of any of the foregoing embodiments, wherein the polypeptides are present in a cell-free system.

The disclosure also provides a recombinant polypeptide comprising a sequence that is at least 95% identical to SEQ ID NO:6 and comprises D34A/L35R/T36K mutations and has glyceraldehyde-3-phosphate dehydrogenase activity.

The disclosure provide a molecular rheostat switch that allows a metabolic system to preferentially proceed down one of two pathways depending upon cofactor balance. For example, in one embodiment, the pathway proceed down an enzyme path that doesn't produce ATP or one that does produce ATP depending upon the amount of free phosphate (Pi) in the system. The choice is regulated by free phosphate which is needed by the mGAP enzyme. Free phosphate is a proxy for the amount of ATP hydrolyzed to ADP in the system. Effectively the flow down the ATP generating pathway is turned up or down depending on the Pi concentration. The biochemical pathway can be used to produced various chemical and biofuels from a carbon source (e.g., glucose).

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

FIG. 4A-D shows a Copasi model of the rheostat pathway with ATPase activity modeled (A-B) and a Copasi model of the stoichiometric pathway with ATPase activity modeled (C-D). The initial conditions are set with 4 mM inorganic phosphate, gapDH M6/PGK activity held constant, and ATP hydrolysis was increased until the reaction died out. The reaction dies at an ATP hydrolysis to gapDH M6 ratio anything higher than 5:1.

FIG. 6A-B provide detailed schematic of the stoichiometric pathway and rheostat pathway.

DETAILED DESCRIPTION

Figure 1:
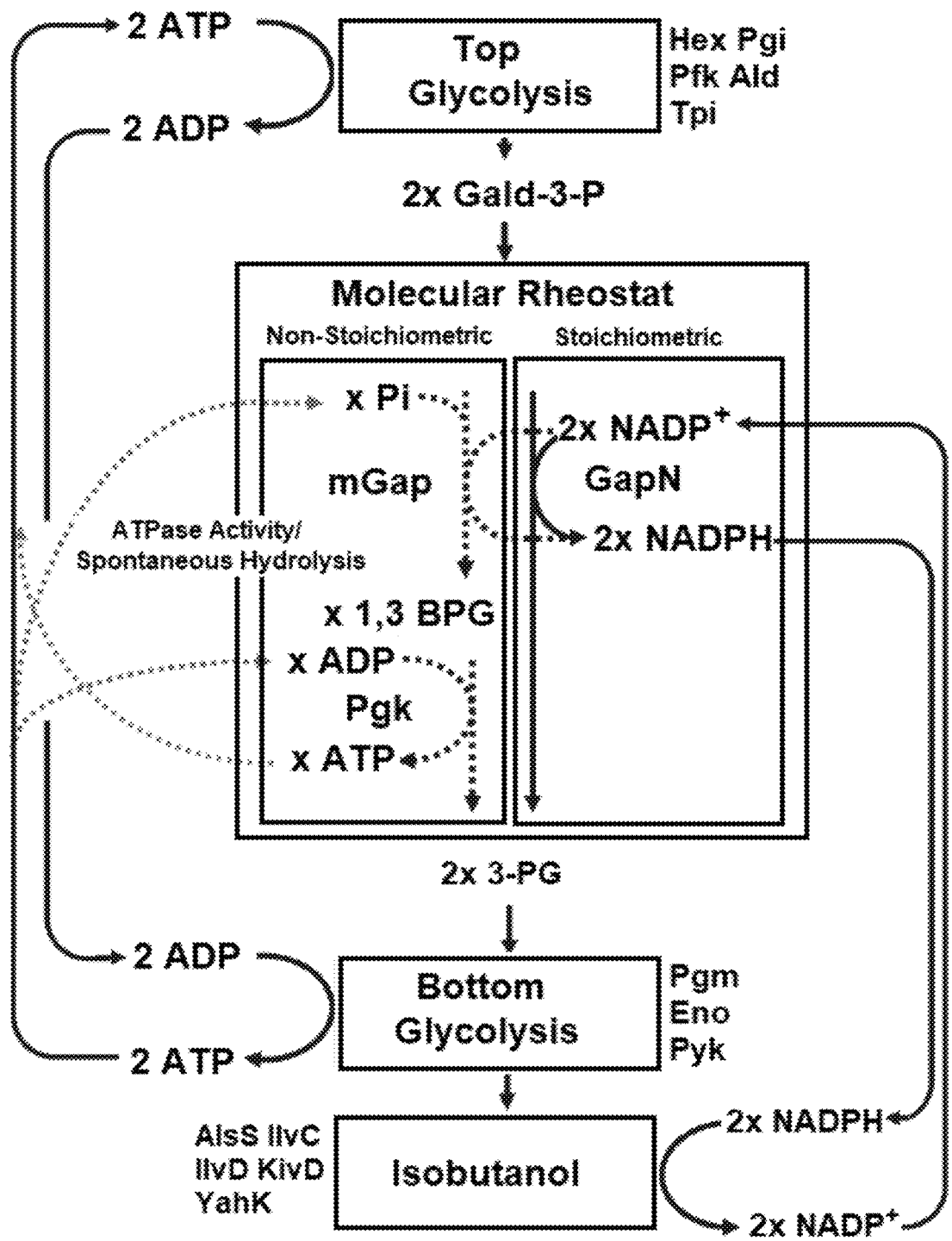
FIG. 1 provides a diagram of an in vitro pathway from glucose to isobutanol. The gapDH M6 and PGK scavenge inorganic phosphate and remake ATP that has been hydrolyzed in the system.

As used herein and in the appended claims, the singular forms "a," "and," and "the" include plural referents unless the context clearly dictates otherwise. Thus, for example, reference to "a polynucleotide" includes a plurality of such polynucleotides and reference to "the enzyme" includes reference to one or more enzymes, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

As used herein, an "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

The term "biosynthetic pathway", also referred to as "metabolic pathway", refers to a set of anabolic or catabolic biochemical reactions for converting (transmuting) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product. The disclosure provides in vitro biosynthetic pathways comprising a molecular rheostat which can optionally include a metabolic purge valve for the production of a desired product or intermediate. The disclosure also provides recombinant microorganism having a metabolically engineered pathway comprising a molecular rheostat and may further comprise a metabolic purge valve for the production of a desired product or intermediate.

As used herein a "cofactor" generally refers to a chemical compound or metabolite that is required for a protein's biological activity. The proteins are commonly enzymes, and cofactors assist in biochemical transformations. Cofactors include, but are not limited to, one or more inorganic ions, or a complex organic or metalloorganic molecule sometimes referred to as a coenzyme; most of which are derived from vitamins and from required organic nutrients in small amounts. Some enzymes or enzyme complexes require several cofactors. For example, the multienzyme complex pyruvate dehydrogenase at the junction of glycolysis and the citric acid cycle requires five organic cofactors and one metal ion: loosely bound thiamine pyrophosphate (TPP), covalently bound lipoamide and flavin adenine dinucleotide (FAD), and the cosubstrates nicotinamide adenine dinucleotide ($NAD^+$) and coenzyme A (CoA), and a metal ion ($Mg^{2+}$). Organic cofactors are often vitamins or are made from vitamins. Many contain the nucleotide adenosine monophosphate (AMP) as part of their structures, such as ATP, coenzyme A, FAD, and $NAD^+$.

An "enzyme" means any substance, typically composed wholly or largely of amino acids making up a protein or polypeptide that catalyzes or promotes, more or less specifically, one or more chemical or biochemical reactions.

The term "expression" with respect to a gene or polynucleotide refers to transcription of the gene or polynucleotide and, as appropriate, translation of the resulting mRNA transcript to a protein or polypeptide. Thus, as will be clear from the context, expression of a protein or polypeptide results from transcription and translation of the open reading frame.

A "metabolite" refers to any substance produced by metabolism or a substance necessary for or taking part in a particular metabolic process that gives rise to a desired metabolite, chemical, alcohol or ketone. A metabolite can be an organic compound that is a starting material (e.g., a carbohydrate, a sugar phosphate, pyruvate etc.), an intermediate in (e.g., acetyl-coA), or an end product (e.g., isobutanol, isoprene or PHB) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

As used herein, the term "metabolically engineered" or "metabolic engineering" involves rational pathway design and assembly of biosynthetic genes, genes associated with operons, and control elements of such polynucleotides, for the production of a desired metabolite, such as acetyl-CoA, higher alcohols or other chemical, in a microorganism, or in a cell-free system the rational pathway design and assembly of a biosynthetic pathway and co-factors for the production of a desired metabolite. "Metabolically engineered" can further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway. For example, in a cell free system a host cell expressing one or more enzymes used in the cell-free sytem can be further engineered to eliminate or remove competing pathway enzymes thereby removing contaminants or enzymes that may be present in a disrupted or cell-free preparation.

A biosynthetic gene can be heterologous to the host microorganism, either by virtue of being foreign to the host, or being modified by mutagenesis, recombination, and/or association with a heterologous expression control sequence in an endogenous host cell. In one embodiment, where the polynucleotide is xenogenetic to the host organism, the polynucleotide can be codon optimized.

A "metabolic purge valve" refers to an engineered metabolic pathway that 'purges' excess metabolites and/or co-factors resulting in a recycling of the metabolite or co-factor for use in a primary metabolic pathway, e.g., by oxidizing a reduced cofactor thus "purging an abundance of reduced cofactors" etc.

Figure 3A:
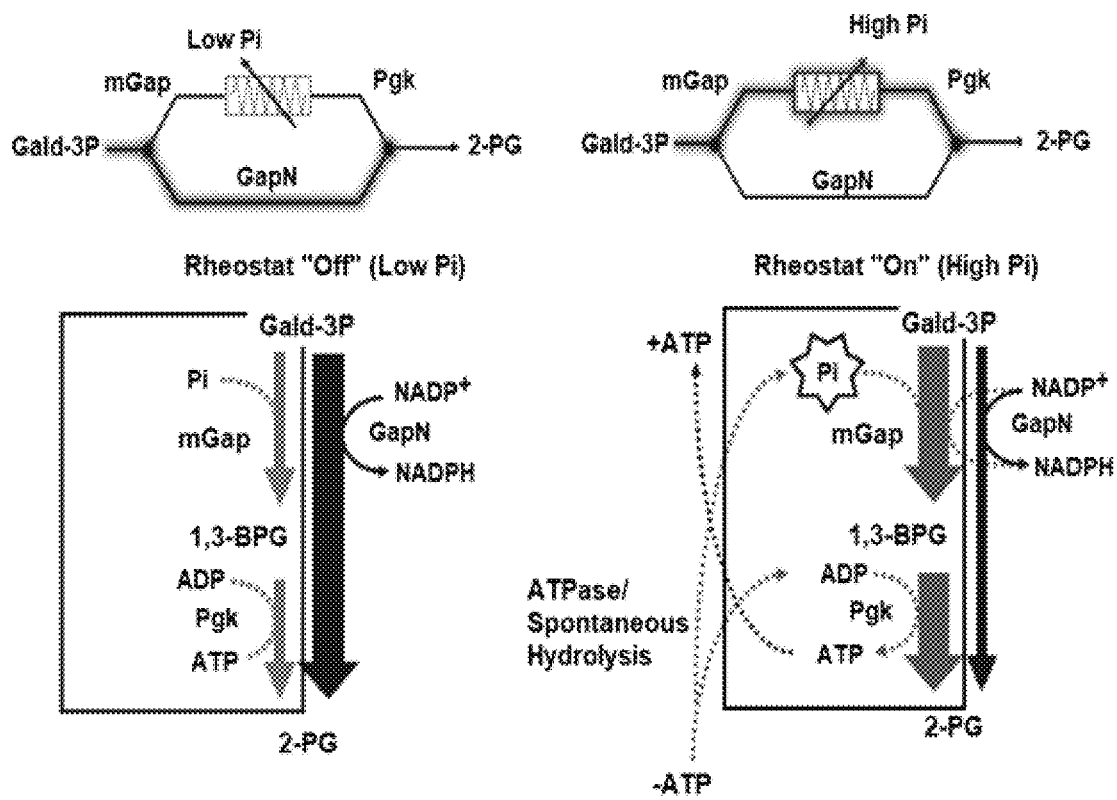
FIG. 3A-B shows a design of the "molecular rheostat" at glyceraldehyde-3-phosphate dehydrogenase. (A) Schematic of the molecular rheostat in glycolysis. (B) Model of the gapDH M6 crystal structure.
Figure 3B:
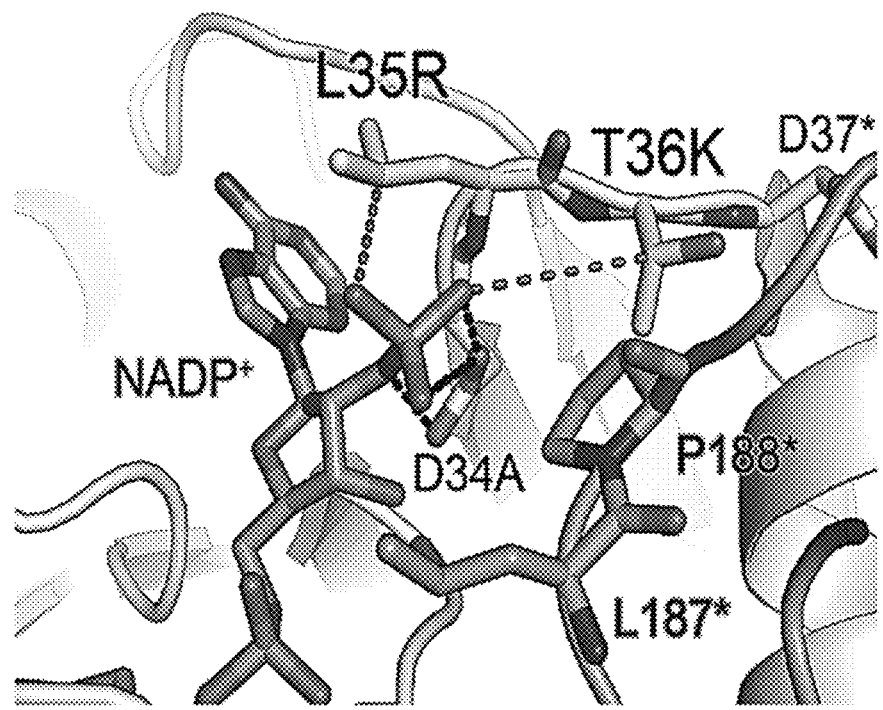

A "molecular rheostat" refers to an enzymatic step that is only activated when a co-factor is at a level sufficient to turn-over the enzyme. In the absence of sufficient levels, the pathway proceeds by a secondary enzymatic step. For example, as shown in FIG. 1, a molecular rheostat can be made up of two competing pathway branches that eventually transform glyceraldehyde-3 phosphate (G3P) into 3-phosphoglycerate (3PG). One branch reduces a cofactor in the conversion of G3P which is regulated by oxidation/reduction levels, while the other branch generates ATP, while flow through the ATP generating branch is regulated by Pi levels. The first branch is made up of one enzyme, the non-phosphorylating GapN used in the stoichiometric pathway, which reduces $NADP^+$ to NADPH and converts G3P directly into 3PG without generating ATP. The second pathway is composed of two enzymes, an NADPH specific, phosphorylating glyceraldehyde-3-phosphate dehydrogenase (GapDH) and phosphoglycerate kinase (PGK), that also produces NADPH but first converts G3P into 1,3-bisphosphoglycerate (1,3BPG) followed by 3PG and ATP by the action of PGK. Therefore, the GapDH/PGK branch produces an additional ATP compared to the GapN only branch. The relative flow through the ATP generating branch of the rheostat is controlled by free Pi, which acts as a proxy for the amount of ATP hydrolyzed to ADP and Pi. The function of the rheostat is depicted in the simplest case, where no exogenous Pi is added to the reaction (FIG. 3A, left panel). In this case there is initially no free Pi and there can be no flux through the phosphorylating GAPDH. Thus, in the absence of Pi, all the flux passes through GapN branch. However, when ATP is hydrolyzed to ADP and Pi, the phosphorylating branch is then utilized. Thus, the rheostat senses the depletion of ATP and acts to restore ATP by utilizing the phosphorylating GAPDH branch (FIG. 3A, right panel).

The term "polynucleotide," "nucleic acid" or "recombinant nucleic acid" refers to polynucleotides such as deoxyribonucleic acid (DNA), and, where appropriate, ribonucleic acid (RNA).

A "protein" or "polypeptide", which terms are used interchangeably herein, comprises one or more chains of chemical building blocks called amino acids that are linked together by chemical bonds called peptide bonds. A protein or polypeptide can function as an enzyme.

The term "recombinant microorganism" and "recombinant host cell" are used interchangeably herein and refer to microorganisms that have been genetically modified to express non-expressed or over-express endogenous polynucleotides, or to express non-endogenous sequences, such as those included in a vector. The polynucleotide generally encodes a target enzyme involved in a metabolic pathway for producing a desired metabolite as described herein, but may also include protein factors necessary for regulation or activity or transcription. Accordingly, recombinant microorganisms described herein have been genetically engineered to express or over-express target enzymes not previously expressed or over-expressed by a parental microorganism. It is understood that the terms "recombinant microorganism" and "recombinant host cell" refer not only to the particular recombinant microorganism but to the progeny or potential progeny of such a microorganism. It should also be understood that the recombinant microorganism can be used as a source of the polypeptide and that the recombinant microorganism need not have the full pathway for the generation of a desired metabolite. Rather, a plurality of recombinant microorganisms each having one or more, but not all, of the polypeptide for a metabolic pathway can be cocultured to produce the desired metabolite or can be disrupted and the cell-free milieu used or the expressed polypeptide isolated from each of the recombinant microorganisms.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, but also intermediate and end product metabolites used in a pathway as described herein. In addition, a substrate can be an oxidized or reduced co-factor or a factor that is phosphorylated or de-phosphorylated.

Metabolic engineering and synthetic biology have been employed for the production of high value chemicals but have not been as successful as hoped in meeting the stringent economics of large scale commodity chemical manufacturing. Microbial systems are often hampered by a variety of technical challenges that make it hard to achieve cost competitiveness, including poor yields due to competing pathways; low productivity caused by slow growth rates or difficulties in pathway optimization; contaminating microbial growth; product toxicity; and expensive product isolation.

As demonstrated herein, one approach to overcome these difficulties is to perform complex biochemical transformations using mixtures of enzymes in a reaction vessel or flow system rather than within a cell. Building single, dedicated pathways in vitro can eliminate side reactions that occur in the cell, so that nearly 100% yields and fast reaction times are possible. In vitro biochemical systems also allow for more precise control over optimization and product toxicity problems can be more easily diagnosed and mitigated. Moreover, product extraction can be more facile.

Traditionally, in vitro pathway construction has been relegated to use as a research tool or in applications that require only 1-3 enzymes for the production of chiral compounds and other high value chemicals. Improvements in protein expression and access to stable enzymes have made more complex systems possible. In vitro biotransformation systems have been reported in recent years involving systems of over thirty enzymes. One of the first modern studies in this area was an artificial pathway that produced hydrogen from starch. The concept was recently advanced with a creative system that generated hydrogen from cellobiose at nearly 100% yields. In another effort, hyper-thermophilic glycolysis enzymes were heterologously expressed, heat purified, and assembled to convert glucose to n-butanol in 82% yield. In another study, an elegantly simplified non-phosphorylative Entner-Doudoroff pathway from hyper-thermophilic archaea was constructed to produce ethanol and isobutanol in ~55% yields. These pioneering studies illustrate the flexibility of synthetic biochemistry and the potential for high yields.

Maintaining proper cofactor balance is an essential part of generating flux and providing a driving force through an enzymatic pathway. In vivo, the enzymatic specificity for the cofactors NADH/NADPH and/or ADP/ATP are typically used to control the carbon flux through catabolic and anabolic pathways respectively. Organisms typically sense the reduction state of these cofactors and use this information to up-regulate or down-regulate catabolic and anabolic pathways to cope with environmental changes. In vitro systems, however, do not have the myriad of peripheral pathways that facilitate this control. Moreover, the natural anabolic and catabolic specificities for NADH and NADPH complicate in vitro biotransformations. Synthetic biochemistry systems have often dealt with these problems by careful considerations of cofactor stoichiometry in pathway design, through the use of expensive sacrificial metabolites, reengineering enzymes so that only a single cofactor type is needed, adding excess cofactors, or constantly adding intermediates to the reaction mix to sustain the process.

Although the methods, compositions and systems described herein are described with reference to certain metabolic products, the methods, compositions and systems are applicable to a broad range of recombinant biochemical pathways where co-factor recycling is important. In one exemplary engineered pathway the disclosure describes the production of isobutanol (see, e.g., FIGS. 1, 6A and 6B).

The disclosure describes a molecular rheostat system for co-factor balance in in vitro pathways for chemical production and in vivo systems. For example, the disclosure describes a pathway to convert glucose into isobutanol that maintains sustainable reducing cofactor balance, without the requirement for perfect stoichiometric matching of cofactor generation and usage to carbon usage.

The disclosure provides a robust node of control to balance the production and consumption of cofactors such as NADPH and NADH and ATP and ADP in a self-regulating and self-balancing manner. This in vitro pathway maintains cofactor balance without requiring adherence to stoichiometry in the generation and utilization of cofactors to ensure carbon flux. In part because the system can switch between enzymatic steps based upon co-factor levels, driving the transformation to near completion.

Ultimately the methods and compositions of the disclosure can be expanded to incorporate the conversion of low cost substrates such as glucose or other sugars into useful chemicals and biofuels.

The disclosure demonstrates the design and use of a self-regulating synthetic biochemical pathways over the standard stoichiometric design using a cell free enzymatic pathway. In the production of isobutanol, the exemplary pathway described herein, the non-rheostat pathway produced about 12 g/L of isobutanol before the reaction stopped due to ATP depletion. Using the rheostat of the disclosure the system can produce an excess of ATP when needed and improved the final titer to 24 g/L.

Synthetic biochemistry systems that do not rely of perfect stoichiometry can run longer and are more flexible because cofactor stoichiometry is not constrained. The disclosure also contemplates the use of molecular purge valves in combination wih the rheotstat of the disclosure. For example, International application publication no. WO2015/153929 and International application No. PCT/US2016/043260 described such purge valve systems (the disclosure of which are incorporated herein by reference). Together, with the ATP regulatory system described here, these synthetic pathways allow for the design of self-sustaining in vitro pathways to a myriad of bio-based products that require balancing both NAD(P)/NAD(P)H and ATP individually or at the same time. These self-regulatory nodes, which can control ATP and NAD(P)/NAD(P)H, provides tools and pahways for industrial cell free enzymatic synthesis.

In one embodiment, a pathway of the disclosure provide parallel enzymatic step that utilize $NADP^+/NADPH$ in a first pathway at low Pi and a second pathway that utilizes $NADP^+/NADPH$ and ADP-ATP cycling at higher Pi.

The disclosure provides pathways that can be developed in vitro in a number of ways. For example, the desired enzymes can be cloned/engineered into a microorganism or cell, expressed and then purified from the culture. In another example, the enzymes can be expressed, the cells disrupted and a disrupted preparation used in the pathways of the disclosure. In another embodiment, the enzymes can be purified and tethered to a substrate in a system (e.g., in a microfluidic system) for use in the metabolic pathway. In yet another embodiment, thermophilic enzymes having the desired activity can be cloned, expressed and the cell or preparations therefrom heated to a temperature wherein the desired enzymes remain active while undesired enzymes are denatured. In yet another embodiment, the enzymes can be commercially purchased and mixed as appropriate. In all of the foregoing embodiments, the system would be combined with the necessary substrates and cofactors (e.g., $NAD^-$, $NADP^-$, $FAD^-$, AMP, ADP, ATP and the like).

Accordingly, the disclosure provides "engineered" or "modified" microorganisms that are produced via the introduction of genetic material into a host or parental microorganism of choice thereby modifying or altering the cellular physiology and biochemistry of the microorganism. Through the introduction of genetic material the parental microorganism acquires new properties, e.g. the ability to produce a new, or greater quantities of, an intracellular metabolite. The genetic material introduced into the parental microorganism contains gene(s), or parts of gene(s), coding for one or more of the enzymes involved in a biosynthetic pathway and include gene(s), or parts of gene(s), coding for one or more of the enzymes involved in a molecular rheostate alone or in combination with metabolic purge valve, the pathway(s) useful for the production of a desired metabolite (e.g., isobutanol), and may also include additional elements for the expression and/or regulation of expression of these genes, e.g. promoter sequences.

An engineered or modified microorganism can also include in the alternative or in addition to the introduction of a genetic material into a host or parental microorganism, the disruption, deletion or knocking out of a gene or polynucleotide to alter the cellular physiology and biochemistry of the microorganism. Through the reduction, disruption or knocking out of a gene or polynucleotide the microorganism acquires new or improved properties (e.g., the ability to produce a new or greater quantities of an intracellular metabolite, improve the flux of a metabolite down a desired pathway, and/or reduce the production of undesirable by-products). For example, it may be desirable to engineer an organism to express a desired set for enzymes in a metabolic pathway while eliminating enzymes of competing pathways. This engineering can be applicable for both in vitro (where upon disruption or purification undesirable enzymes are not present) or in vivo.

A "native" or "wild-type" protein, enzyme, polynucleotide, gene, or cell, means a protein, enzyme, polynucleotide, gene, or cell that occurs in nature.

A "parental microorganism" refers to a cell used to generate a recombinant microorganism. The term "parental microorganism" describes, in one embodiment, a cell that occurs in nature, i.e. a "wild-type" cell that has not been genetically modified. The term "parental microorganism" further describes a cell that serves as the "parent" for further engineering. In this latter embodiment, the cell may have been genetically engineered, but serves as a source for further genetic engineering.

For example, a wild-type microorganism can be genetically modified to express or over express a first target enzyme such as a NADH-pyruvate dehydrogenase. This microorganism can act as a parental microorganism in the generation of a microorganism modified to express or over-express a second target enzyme. As used herein, "express" or "over express" refers to the phenotypic expression of a desired gene product. In one embodiment, a naturally occurring gene in the organism can be engineered such that it is linked to a heterologous promoter or regulatory domain, wherein the regulatory domain causes expression of the gene, thereby modifying its normal expression relative to the wild-type organism. Alternatively, the organism can be engineered to remove or reduce a repressor function on the gene, thereby modifying its expression. In yet another embodiment, a cassette comprising the gene sequence operably linked to a desired expression control/regulatory element is engineered in to the microorganism.

Accordingly, a parental microorganism functions as a reference cell for successive genetic modification events. Each modification event can be accomplished by introducing one or more nucleic acid molecules in to the reference cell. The introduction facilitates the expression or over-expression of one or more target enzyme or the reduction or elimination of one or more target enzymes. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of exogenous polynucleotides encoding a target enzyme in to a parental microorganism.

Polynucleotides that encode enzymes useful for generating metabolites including homologs, variants, fragments, related fusion proteins, or functional equivalents thereof, are used in recombinant nucleic acid molecules that direct the expression of such polypeptides in appropriate host cells, such as bacterial or yeast cells.

It is understood that a polynucleotide described herein include "genes" and that the nucleic acid molecules described above include "vectors" or "plasmids." Accordingly, the term "gene", also called a "structural gene" refers to a polynucleotide that codes for a particular polypeptide comprising a sequence of amino acids, which comprise all or part of one or more proteins or enzymes, and may include regulatory (non-transcribed) DNA sequences, such as promoter region or expression control elements, which determine, for example, the conditions under which the gene is expressed. The transcribed region of the gene may include untranslated regions, including introns, 5'-untranslated region (UTR), and 3'-UTR, as well as the coding sequence.

Those of skill in the art will recognize that, due to the degenerate nature of the genetic code, a variety of codons differing in their nucleotide sequences can be used to encode a given amino acid. A particular polynucleotide or gene sequence encoding a biosynthetic enzyme or polypeptide described above are referenced herein merely to illustrate an embodiment of the disclosure, and the disclosure includes polynucleotides of any sequence that encode a polypeptide comprising the same amino acid sequence of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate exemplary embodiments of the disclosure.

The disclosure provides polynucleotides in the form of recombinant DNA expression vectors or plasmids, as described in more detail elsewhere herein, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) form.

A polynucleotide of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated polynucleotide molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitution, in some positions it is preferable to make conservative amino acid substitutions.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

"Transformation" refers to the process by which a vector is introduced into a host cell. Transformation (or transduction, or transfection), can be achieved by any one of a number of means including electroporation, microinjection, biolistics (or particle bombardment-mediated delivery), or *agrobacterium* mediated transformation.

A "vector" generally refers to a polynucleotide that can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For E. coli and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433, which is incorporated herein by reference in its entirety), can also be used. For E. coli expression vectors, it is useful to include an E. coli origin of replication, such as from pUC, p1P, p1, and pBR.

Thus, recombinant expression vectors contain at least one expression system, which, in turn, is composed of at least a portion of a gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

In addition, and as mentioned above, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

In some instances "isozymes" can be used that carry out the same functional conversion/reaction, but which are so dissimilar in structure that they are typically determined to not be "homologous".

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which can also be referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

In certain embodiments, a metabolic pathway converts a carbon source to a desired intermediate or end product. For example, a carbon source can be converted to pyruvate, which can be metabolized to acetyl-CoA or to isobutanol. Suitable carbon sources can be sugars. For example, a carbon source can be a biomass derived sugar. A "biomass derived sugar" includes, but is not limited to, molecules such as glucose, sucrose, mannose, xylose, and arabinose. The term biomass derived sugar encompasses suitable carbon substrates of 1 to 7 carbons ordinarily used by microorganisms, such as 3-7 carbon sugars, including but not limited to glucose, lactose, sorbose, fructose, idose, galactose and mannose all in either D or L form, or a combination of 3-7 carbon sugars, such as glucose and fructose, and/or 6 carbon sugar acids including, but not limited to, 2-keto-L-gulonic acid, idonic acid (IA), gluconic acid (GA), 6-phosphogluconate, 2-keto-D-gluconic acid (2 KDG), 5-keto-D-gluconic acid, 2-ketogluconatephosphate, 2,5-diketo-L-gulonic acid, 2,3-L-diketogulonic acid, dehydroascorbic acid, erythorbic acid (EA) and D-mannonic acid.

Cellulosic and lignocellulosic feedstocks and wastes, such as agricultural residues, wood, forestry wastes, sludge from paper manufacture, and municipal and industrial solid wastes, provide a potentially large renewable feedstock for the production of chemicals, plastics, fuels and feeds. Cellulosic and lignocellulosic feedstocks and wastes, composed of carbohydrate polymers comprising cellulose, hemicellulose, and lignin can be generally treated by a variety of chemical, mechanical and enzymatic means to release primarily hexose and pentose sugars. These sugars can then be "fed" into a pathway to produce pyruvate as further described herein.

The disclosure provides accession numbers for various genes, homologs and variants useful in the generation of recombinant microorganism described herein. It is to be understood that homologs and variants described herein are exemplary and non-limiting. Additional homologs, variants and sequences are available to those of skill in the art using various databases including, for example, the National Center for Biotechnology Information (NCBI) access to which is available on the World-Wide-Web.

Culture conditions suitable for the growth and maintenance of a recombinant microorganism provided herein are known in the art.

It is understood that a range of microorganisms can be engineered to express one or more enzymes of the disclosure. It is also understood that various microorganisms can act as "sources" for genetic material encoding target enzymes suitable for use in a recombinant microorganism provided herein.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the procaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt ([NaCl]); and extreme (hyper) thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; and (11) *Thermotoga* and Thermosipho thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The disclosure provides a molecular rheostat for controlling ATP levels in an in vitro or in vivo system that comprises the metabolite conversion of glyceraldehyde-3-phosphate to 3-phosphoglycerate. The molecular rheostat the expression or over expression of heterologous polynucleotide or over-expression of native polynucleotides, or an enzymatic in vitro system comprising (i) an enzyme that converts glyceraldehyde-3-phosphate (G3P) and $NADP^+$ to 3-phosphoglycerate (3PG) and NADPH and (ii) an enzyme that converts glyceraldehyde-3-phosphate (G3P), $NADP^+$ and free phosphate (Pi) to 1,3-bisphosphoglycerate (1,3BPG) and (iii) an enzyme that converts 1,3 bisphosphglycerate (1,3BPG) and ADP to 3-phophoglycerate and ATP. In one embodiment, the enzyme of (i) comprises a NADP-dependent glyceraldehyde-3-phosphate dehydrogenase (GapN). In a further embodiment, the GapN is obtained from *S. mutans*. In another embodiment, the enzyme of (ii) comprises a mutant glyceraldehyde-3-phosphate dehydrogenase (mGap) that comprises D34A/L35R/T36K mutations relative to wild-type (SEQ ID NO:6). In another embodiment, the enzyme of (iii) comprises enzyme commission number (EC number) EC 2.7.2.3. In a further embodiment, the enzyme is a phosphoglycerate kinase. In still another embodiment, the phosphoglycerate kinase is a Pgk from *G. stearothermophilus*. In another embodiment, the molecular rheostat comprise the enzymes of a NADP-dependent glyceraldehyde-3-phosphate dehydrogenase (GapN), a mutant glyceraldenhyde-3-phosphate dehydrogenase that utilizes $NADP^+$ and a phosphglycerate kinase.

In another embodiment, the disclosure demonstrates the production of isobutanol using a molecular rheostat. The pathway comprises the expression or over expression of one or more heterologous polynucleotide or over-expression of one or more native polynucleotides, or an enzymatic in vitro system comprising (i) a polypeptide that catalyzes the production of glucose-6-phosphate (G6P) from glucose; (ii) a polypeptide that catalyzes the production of Fructose-6-phosphate (F6P) from glucose-6-phosphate (G6P); (iii) a polypeptide the catalyzes the conversion/phosphorylation of fructose-6-phosphate (F6P) to fructose-1,6-phosphate (iv) a polypeptide that converts fructose-1,6-phosphate to two glyceraldehyde-3-phosphates (G3P); (v) a molecular rheostat comprising (a) an enzyme that converts glyceraldehyde-3-phosphate (G3P) and $NADP^+$ to 3-phosphoglycerate (3PG) and NADPH and (b) an enzyme that converts glyceraldehyde-3-phosphate (G3P), $NADP^+$ and free phosphate (Pi) to 1,3-bisphosphoglycerate (1,3BPG) and (c) an enzyme that converts 1,3 bisphosphglycerate (1,3BPG) and ADP to 3-phophoglycerate (3pG) and ATP; (vi) a polypeptide that converts 3-phosphoglycerate (3PG) to 2-phosphoglycerate (2PG); (vii) a polypeptide that converts 2-phosphoglycerate (2PG) to phosphoenolpyruvate (PEP); (viii) a polypeptide that converts phosphoenolpyruvate (PEP) to pyruvate; (ix) a polypeptide that converts pyruvate to acetolactate; (x) a polypeptide that converts acetolactate and NADPH to 2,3 dihydroxy-3-methyl butanoate and $NADP^+$; (xi) a polypeptide that converts 2,3 dihydroxy-3-methyl butanoate to 3-methyl-2-oxobutanoate; (xii) a polypeptide that converts 3-methyl-2-oxobutanoate to isobutanal and (xiii) a polypeptide that coverts isobutanal to isobutanol.

It will be recognized by one of skill in the art that the various metabolites identified above can serve as substrate for other catabolic or anabolic pathways.

Accordingly, the disclosure provides systems and recombinant microorganisms that can produce acetyl-phosphate, pyruvate, glyceraldehyde-3-phosphate, acetyl-CoA and/or other metabolites derived therefrom wherein the system or microorganism comprises a molecular rheostat or a molecular rheostat and a purge valve. For example, the disclosure provides pathways that can comprise a molecular rheostat and one or more enzyme selected from a glucokinase (Glk or variant of homolog thereof, including a polyphosphate-dependent glucokinase, pfkA), a phosphoketolase (e.g., Fpk, Xpk, or Fpk/Xpk or variant of homolog thereof), a transaldolase (e.g., Tal or variant thereof), a transketolase (e.g., Tkt or variant of homolog thereof), ribose-5-phosphate isomerase (e.g., Rpi or variant of homolog thereof), a ribulose-5-phosphate epimerase (e.g., Rpe or variant of homolog thereof), a triose phosphate isomerase (e.g., Tpi or variant of homolog thereof), a fructose 1,6 bisphosphate aldolase (e.g., Fba or variant of homolog thereof), a phosphoglucoisomerase (e.g., Pgi or variant of homolog thereof), an enolase, a decarboxylase (e.g., KivD or homolog), an alcohol dehydrogenase (e.g., an NADPH dependent alcohol dehydrogenase such as YahK or homolog), a phosphoglucoisomerase (e.g., Pgi or homolog), a fructose 1,6 bisphosphate isomerase (Fba or homolog thereof), a phophoglycerate mutase (e.g., Pgk or homolog thereof), a pyruvate kinase (Pyk or homolog thereof), a ketol-acid reductoisomerase (IlvC or homolog thereof), a dihydroxy-acid dehydratase (e.g., IlvD or homolog thereof) and any combination thereof. Table 1 provides a list of accession number and organism that can be used as source sources of the enzymes:

TABLE 1

Enzymes and Sources:

| Enzyme | Name | Accession number | Source Organism |
| --- | --- | --- | --- |
| Sc Hk | Hexokinase | — | *S. Cerevisiae* |
| Gt PgiA | Phosphoglucoisomerase | ABO68222 | *G. thermodenitrificans* NG80-2 |
| Gs PfkA | Phosphoglucokinase | KOR92562 | *G. stearothermophilus* ATCC12980 |
| Sa FBA | Fructose 1,6 biphosphate aldolase | BAR10119 | *S. aureus* subsp. *Aureus* |
| Gs TPI | Triose Phosphate isomerase | KOR95273 | *G. stearothermophilus* ATCC12980 |
| Sm GapN | Non-phosphorylating Glyceraldehyde 3 | NP_J721104 | *S. mutans* |

TABLE 1-continued

Enzymes and Sources:

| Enzyme | Name | Accession number | Source Organism |
|---|---|---|---|
| | phosphate dehydrogenase Phosphorylating | | |
| Gs mGapDH | Glyceraldehyde-3-phosphate Dehydrogenase | WP_033015082 | G. stearothermophilus ATCC12980 |
| Gs PGK | Phophoglycerate Kinase | WP_033015089 | G. stearothermophilus ATCC12980 |
| Gs PGM | Phosphoglycerate Mutase | KOR95274 | G. stearothermophilus ATCC12980 |
| Ec Enolase | Enolase | NP_417259 | E. coli K12 sp MG1655 |
| Ec PykF | Pyruvate Kinase | NP_416191 | E. coli K12 sp MG1655 |
| Bs AlsS | Acetolactate Synthase | NP_391482 | B. Subtilis subtilis 168 |
| Ec IlvC | Ketol-Acid Reductoisomerase | AKK14493 | E. coli K12 sp MG1655 |
| Re IlvD | Dihydroxy-Acid Dehydratase | Q0K4J3 | R. eutropha |
| Ll KlvD | Keto-Isovalerate Decarboxylase | CAG34226 | L. lactis subsp. Lactis |
| Ec YahK | Alcohol Dehydrogenase | NC_000913.3 | E. coli K12 |

The foregoing one or more enzymes can be used in combination with enzymes that catalyze the conversion of glyceraldehyde-3-phosphate to 3-phosphoglycerate with or without an intermediate step of conversion to 1,3-bisphosphoglycerate, wherein the intermediate step is regulated by the level of phosphate.

In addition, a microorganism may include a disruption, deletion or knockout of expression of an alcohol/acetoaldehyde dehydrogenase that preferentially uses acetyl-coA as a substrate (e.g. adhE gene), as compared to a parental microorganism. In some embodiments, further knockouts may include knockouts in a lactate dehydrogenase (e.g., ldh) and frdBC. In other embodiments, knockouts or reductions in expression or activity of one or more of gapA, eda, edd and mgsA may be performed to remove other glycolysis pathways in the microorganism. Other enzymes that can be knocked out or expression reduced include Fbp, glpX, and homologs and variants thereof.

It will be recognized that subsystems or organism that have one or more (but not all) of the foregoing enzymes can be utilized and then combined with an organism or other subsystems comprising remaining enzymatic members of the pathway.

As previously noted, the target enzymes described throughout this disclosure generally produce metabolites. In addition, the target enzymes described throughout this disclosure are encoded by polynucleotides.

Accordingly, in one embodiment, a system or recombinant microorganism provided herein comprises a glucokinase (Glk, polyphosphate-dependent glucokinase or homolog or variant thereof). This expression may be combined with enzymes of the molecular rheostat and may further include additional downstream enzymes for the production of a desired metabolite. The Glk can be derived from G. stearothermophilus. In another embodiment, an engineered variant of Glk can be used so long as it has glucokinase activity and can convert glucose to glucose-6-phosphate. Such engineered variants can be obtained by site-directed mutagenesis, directed evolutions and the like. Thus included within the disclosure are polypeptides that are at least 85-99% identical to the sequence of Glk from E. coli and having glucokinase activity.

In another or further embodiment, a system or recombinant microorganism provided herein includes expression of a phosphofructokinase (Pfk, polyphosphate-dependent Pfk or homolog or variants thereof). This expression may be combined with other enzymes in the metabolic pathway for the production of acetyl-phosphate, acetyl-coA or other metabolites derived therefrom. The Pfk can be derived from G. stearothermophilus. In another embodiment, an engineered variant of Pfk can be used so long as it has phosphoglucokinase and/or phosphofructokinase activity and can convert fructose-6 phosphate to fructose-1,6-phosphate. Such engineered variants can be obtained by site-directed mutagenesis, directed evolutions and the like. Thus included within the disclosure are polypeptides that are at least 85-99% identical to a sequence Pfk from G. sterothermophilus and having 6-phosphofructokinase activity (e.g., 85-100% identical to SEQ ID NO:1).

In another embodiment, a system or recombinant microorganism provided herein includes a triose phosphate isomerase. This enzyme may be combined with other enzymes in the metabolic pathway for the production of acetyl-phosphate, pyruvate, acetyl-CoA or other metabolites derived therefrom as described herein above and below. The enzyme produces a metabolite that includes glyceraldehyde-3-phosphate from fructose-1,6-phosphate. The triose phosphate isomerase can be encoded by a Tpi gene, polynucleotide or homolog thereof. The Tpi gene or polynucleotide can be derived from various microorganisms including G. stearothermophilus and E. coli.

In addition to the foregoing, the terms "triose phosphate isomerase" or "Tpi" refer to proteins that are capable of catalyzing the formation of glyceraldehyde-3-phosphate from fructose-1,6-phosphate, and which share at least about 40%, 45%, 50%, 55%, 60%, 65%, 70%, 75%, 80%, 85%, 90%, 95%, 96%, 97%, 98%, 99% or greater sequence identity to SEQ ID NO:2, or at least about 50%, 60%, 70%, 80%, 90%, 95%, 96%, 97%, 98%, 99% or greater sequence similarity, as calculated by NCBI BLAST, using default parameters. Additional homologs include: G. stearothermophilus ATCC12980, KOR95273 (SEQ ID NO:2); Rattus norvegicus AAA42278.1; Homo sapiens AAH17917.1; Bacillus subtilis BEST7613 NP 391272.1; Synechococcus

*elongatus* PCC 6301 YP 171000.1; and *Salmonella enterica* subsp. *enterica* serovar *Typhi* str. AG3 ZP_06540375.1. The sequences associated with the foregoing accession numbers are incorporated herein by reference.

In another embodiment, a system or recombinant microorganism provided herein includes a fructose 1,6 bisphosphate aldolase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes glyceraldeyde-3-phosphate from fructose 1,6-bisphosphate. The fructose 1,6 bisphosphate aldolase can be encoded by a Fba gene, polynucleotide or homolog thereof. The Fba gene or polynucleotide can be derived from various microorganisms including *S. aureus*.

In addition to the foregoing, the terms "fructose 1,6 bisphosphate aldolase" or "Fba" refer to proteins that are capable of catalyzing the formation of glyceraldehyde-3-phosphate from fructose 1,6-bisphosphate, and which share at least about 40%, 45%, 50%, 55%, 60%, 65%, 70%, 75%, 80%, 85%, 90%, 95%, 96%, 97%, 98%, 99% or greater sequence identity to SEQ ID NO:3, or at least about 50%, 60%, 70%, 80%, 90%, 95%, 96%, 97%, 98%, 99% or greater sequence similarity, as calculated by NCBI BLAST, using default parameters. Additional homologs include: *S. aureus* subsp. *Aureus*, BAR10119 (SEQ ID NO:3); *Synechococcus elongatus* PCC 6301 YP_170823.1; *Vibrio nigripulchritudo* ATCC 27043 ZP_08732298.1; *Methylomicrobium album* BG8 ZP_09865128.1; *Pseudomonas fluorescens* Pf0-1 YP_350990.1; and *Methylobacterium nodulans* ORS 2060 YP_002502325.1. The sequences associated with the foregoing accession numbers are incorporated herein by reference.

In another embodiment, a system or recombinant microorganism provided herein includes a phosphoglucoisomerase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes fructose-phosphate from glucose-6-phosphate. The phosphoglucokinase can be encoded by a Pgi gene, polynucleotide or homolog thereof. The Pgi gene or polynucleotide can be derived from various microorganisms including *G. thermodenitrificans*.

In addition to the foregoing, the terms "phosphoglucoisomerase" or "Pgi" refer to proteins that are capable of catalyzing the formation of fructose-6-phosphate from glucose-6-phosphate, and which share at least about 40%, 45%, 50%, 55%, 60%, 65%, 70%, 75%, 80%, 85%, 90%, 95%, 96%, 97%, 98%, 99% or greater sequence identity to SEQ ID NO:4, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes a non-phosphorylating glyceraldehyde-3-phosphate dehydrogenase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes 3-phosphoglycerate from glyceraldehyde-3-phosphate. The non-phosphorylating glyceraldehyde-3-phosphate dehydrogenase can be encoded by a GapN gene, polynucleotide or homolog thereof. The GapN gene or polynucleotide can be derived from various microorganisms including *S. mutans*.

In addition to the foregoing, the terms "non-phosphorylating glyceraldehyde-3-phosphate dehydrogenase" or "GapN" refer to proteins that are capable of catalyzing the formation of 3-phosphoglycerate from glyceraldehyde-3-phosphate, and which share at least about 40%, 45%, 50%, 55%, 60%, 65%, 70%, 75%, 80%, 85%, 90%, 95%, 96%, 97%, 98%, 99% or greater sequence identity to SEQ ID NO:5, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes a mutant phophorylating glyceraldehyde-3-phosphate dehydrogenase the preferentially used $NADP^+$. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes 1,3-bisphosphoglycerate from glyceraldehyde-3-phosphate. The mutant phophorylating glyceraldehyde-3-phosphate dehydrogenase can be encoded by mutated from a GapDH gene, polynucleotide or homolog thereof to include mutations D34A/L35R/T36K. The GapDH gene or polynucleotide can be derived from various microorganisms including *G. stearothermophilus*.

In addition to the foregoing, the terms "mutant phophorylating glyceraldehyde-3-phosphate dehydrogenase" or "mGap" refer to proteins that are capable of catalyzing the formation of 1,3-bisphosphoglycerate from glyceraldehyde-3-phosphate and NADP+ and free phosphate (Pi), and which share at least about 40%, 45%, 50%, 55%, 60%, 65%, 70%, 75%, 80%, 85%, 90%, 95%, 96%, 97%, 98%, 99% or greater sequence identity to SEQ ID NO:6 and includes the mutations D34A/L35R/T36K, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes a phosphoglycerate kinase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes 3-phosphoglycerate from 1,3-bisphosphoglycerate and ADP. The phosphoglycerate kinase can be encoded by a Pgk gene, polynucleotide or homolog thereof. The Pgk gene or polynucleotide can be derived from various microorganisms including *G. stearothermophilus*.

In addition to the foregoing, the terms "phosphoglycerate kinase" or "Pgk" refer to proteins that are capable of catalyzing the formation of 3-phosphoglycerate from 1,3-bisphosphoglycerate and ADP, and which share at least about 40%, 45%, 50%, 55%, 60%, 65%, 70%, 75%, 80%, 85%, 90%, 95%, 96%, 97%, 98%, 99% or greater sequence identity to SEQ ID NO:7, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes a phosphoglycerate mutase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes 2-phosphoglycerate from 3-phosphoglycerate. The phosphoglycerate mutase can be encoded by a Pgm gene, polynucleotide or homolog thereof. The Pgm gene or polynucleotide can be derived from various microorganisms including *G. stearothermophilus*.

In addition to the foregoing, the terms "phosphoglycerate mutase" or "Pgm" refer to proteins that are capable of catalyzing the formation of 2-phosphoglycerate from 3-phosphoglycerate, and which share at least about 40%, 45%, 50%, 55%, 60%, 65%, 70%, 75%, 80%, 85%, 90%, 95%, 96%, 97%, 98%, 99% or greater sequence identity to SEQ ID NO:8, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes an enolase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes phosphoenolpyruvate from 2-phosphoglycerate. The enolase can be encoded by an enolase gene, polynucleotide or homolog thereof. The enolase gene or polynucleotide can be derived from various microorganisms including *E. coli*.

In addition to the foregoing, the terms "enolase" refer to proteins that are capable of catalyzing the formation of phospoenolpyruvate from 2-phosphoglycerate, and which share at least about 40%, 45%, 50%, 55%, 60%, 65%, 70%, 75%, 80%, 85%, 90%, 95%, 96%, 97%, 98%, 99% or greater sequence identity to SEQ ID NO:9, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes a pyruvate kinase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes pyruvate from phosphoenolpyruvate. The pyruvate kinase can be encoded by a Pyk gene, polynucleotide or homolog thereof. The Pyk gene or polynucleotide can be derived from various microorganisms including *E. coli*.

In addition to the foregoing, the terms "pyruvate kinase" or "Pyk" refer to proteins that are capable of catalyzing the formation of pyruvate from phosphoenolpyruvate, and which share at least about 40%, 45%, 50%, 55%, 60%, 65%, 70%, 75%, 80%, 85%, 90%, 95%, 96%, 97%, 98%, 99% or greater sequence identity to SEQ ID NO:10, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes an acetolactate synthase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes acetolactate from pyruvate. The acetolactate synthase can be encoded by a AlsS gene, polynucleotide or homolog thereof. The AlsS gene or polynucleotide can be derived from various microorganisms including *B. subtilis*. In one aspect, the acetohydroxy acid synthase may be encoded by a polynucleotide derived from the ilvIH operon, ilvBN operon, ilvGM in *E. coli*, or the alsS gene from *Bacillus subtilis*, or homologs thereof. The ilvI gene of the ilvIH operon encodes an acetohydroxyacid synthase large subunit polypeptide and the ilvH gene of the ilvIH operon encodes an acetohydroxyacid synthase small subunit polypeptide.

In addition to the foregoing, the terms "acetolactate synthase" or "AlsS" refer to proteins that are capable of catalyzing the formation of pyruvate from phosphoenolpyruvate, and which share at least about 40%, 45%, 50%, 55%, 60%, 65%, 70%, 75%, 80%, 85%, 90%, 95%, 96%, 97%, 98%, 99% or greater sequence identity to SEQ ID NO:11, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes an acetohydroxy acid isomeroreductase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes 2,3 dihydroxy-3-methyl butanoate from acetolactate. The acetohydroxy acid isomeroreductase can be encoded by a IlvC gene, polynucleotide or homolog thereof. The IlvC gene or polynucleotide can be derived from various microorganisms including *E. coli*. Acetohydroxy acid isomeroreductase is the second enzyme in parallel pathways for the biosynthesis of isoleucine and valine. IlvC encodes an acetohydroxy acid isomeroreductase in *E. coli*. Homologs and variants of ilvC are known and include, for example, acetohydroxyacid reductoisomerase (*Schizosaccharomyces pombe* 972h−) gi|162312317|ref|NP_001018845.2|(162312317); acetohydroxyacid reductoisomerase (*Schizosaccharomyces pombe*) gi|3116142|emb|CAA18891.1|(3116142); acetohydroxyacid reductoisomerase (*Saccharomyces cerevisiae* YJM789) gi|151940879|gb|EDN59261.1|(151940879); Ilv5p: acetohydroxyacid reductoisomerase (*Saccharomyces cerevisiae*) gi|609403|gb|AAB67753.1|(609403); ACL198Wp (*Ashbya gossypii* ATCC 10895) gi|45185490|ref|NP_983206.1| (45185490); ACL198Wp (*Ashbya gossypii* ATCC 10895) gi|44981208|gb|AAS51030.1|(44981208); acetohydroxyacid isomeroreductase; Ilv5x (*Saccharomyces cerevisiae*) gi|957238|gb|AAB33579.1∥bbm|369068|bbs|165406 (957238); acetohydroxy-acid isomeroreductase; Ilv5g (*Saccharomyces cerevisiae*) gi|957236|gb|AAB33578.1∥bbm|369064|bbs|165405(957236); and ketol-acid reductoisomerase (*Schizosaccharomyces pombe*) gi|2696654|dbj|BAA24000.1|(2696654), each sequence associated with the accession number is incorporated herein by reference.

In addition to the foregoing, the terms "acetohydroxy acid isomeroreductase" or "IlvC" refer to proteins that are capable of catalyzing the formation of pyruvate from phosphoenolpyruvate, and which share at least about 40%, 45%, 50%, 55%, 60%, 65%, 70%, 75%, 80%, 85%, 90%, 95%, 96%, 97%, 98%, 99% or greater sequence identity to SEQ ID NO:12, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes dihydroxy-acid dehydratase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes 3-methyl-2-oxobutanoate from 2,3 dihydroxy-3-methyl butanoate. The dihydroxy-acid dehydratase can be encoded by a IlvD gene, polynucleotide or homolog thereof. The IlvD gene or polynucleotide can be derived from various microorganisms including *E. coli*. Dihydroxy-acid dehydratases catalyzes the fourth step in the biosynthesis of isoleucine and valine, the dehydratation of 2,3-dihydroxy-isovaleic acid into alpha-ketoisovaleric acid. IlvD and ilv3 encode a dihydroxy-acid dehydratase. Homologs and variants of dihydroxy-acid dehydratases are known and include, for example, IlvD (*Mycobacterium leprae*) gi|2104594|emb|CAB08798.1|(2104594); dihydroxy-acid dehydratase (*Tropheryma whipplei* TW08/27) gi|28410848|emb|CAD67234.1|(28410848); dihydroxy-acid dehydratase (*Mycobacterium leprae*) gi|13093837|emb|CAC32140.1|(13093837); dihydroxy-acid dehydratase (*Rhodopirellula baltica* SH 1) gi|32447871|emb|CAD77389.1|(32447871); and putative dihydroxy-acid dehydratase (*Staphylococcus aureus* subsp. *aureus* MRSA252) gi|49242408|emb|CAG41121.1| (49242408), each sequence associated with the accession numbers are incorporated herein by reference.

In addition to the foregoing, the terms "dihydroxy-acid dehydratase" or "IlvD" refer to proteins that are capable of catalyzing the formation of pyruvate from phosphoenolpyruvate, and which share at least about 40%, 45%, 50%, 55%, 60%, 65%, 70%, 75%, 80%, 85%, 90%, 95%, 96%, 97%, 98%, 99% or greater sequence identity to SEQ ID NO:13, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes 2-ketoacid decarboxylase (also referred to as a keto-isovalerate decarboxylase). This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes isobutanal from 3-methyl-2-oxobutanoate. The 2-ketoacid decarboxylase can be encoded by a kivD gene, polynucleotide or homolog thereof. The kivD gene or polynucleotide can be derived from various microorganisms including *L. lactis*. Dihydroxy-acid dehydratases catalyzes the fourth step in the biosynthesis of isoleucine and valine, the dehydratation of 2,3-dihydroxy-isovaleic acid into alpha-ketoisovaleric acid. IlvD and ilv3 encode a dihydroxy-acid dehydratase. 2-ketoacid decarboxylases catalyze the conversion of a 2-ketoacid to the respective aldehyde. For example, 2-ketoisovalerate decarboxylase catalyzes the conversion of 2-ketoisovalerate to isobutyraldehyde. A number of 2-ketoacid decarboxylases are known and are exemplified by the pdc, pdc1, pdc5, pdc6, aro10, thI3, kdcA and kivd genes. Exemplary homologs and variants useful for the conversion of a 2-ketoacid to the respective aldehyde comprise sequences designated by the following accession numbers and identified enzymatic activity: gi|44921617|gb|AAS49166.1| branched-chain alpha-keto acid decarboxylase (*Lactococcus lactis*); gi|15004729|ref|NP_149189.1| Pyruvate decarboxylase (*Clostridium acetobutylicum* ATCC 824); gi|82749898|ref|YP_415639.1| probable pyruvate decarboxylase (*Staphylococcus aureus* RF122); gi|77961217|ref|ZP_00825060.1| COG3961: Pyruvate decarboxylase and related thiamine pyrophosphate-requiring enzymes (*Yersinia mollaretii* ATCC 43969); gi|71065418|ref|YP_264145.1| putative pyruvate decarboxylase (*Psychrobacter arcticus* 273-4); gi|16761331|ref|NP_456948.1| putative decarboxylase (*Salmonella enterica* subsp. *enterica* serovar *Typhi* str. CT18); gi|93005792|ref|YP_580229.11 Pyruvate decarboxylase (*Psychrobacter cryohalolentis* K5); gi|23129016|ref|ZP_00110850.1| COG3961: Pyruvate decarboxylase and related thiamine pyrophosphate-requiring enzymes (*Nostoc punctiforme* PCC 73102); gi|16417060|gb|AAL18557.1|AF354297_1 pyruvate decarboxylase (*Sarcina ventriculi*); gi|15607993|ref|NP_215368.1|PROBABLE PYRUVATE OR INDOLE-3-PYRUVATE DECARBOXYLASE PDC (*Mycobacterium tuberculosis* H37Rv); gi|41406881|ref|NP_959717.1| Pdc (*Mycobacterium avium* subsp. *paratuberculosis* K-10); gi|91779968|ref|YP_555176.1| putative pyruvate decarboxylase (*Burkholderia xenovorans* LB400); gi|15828161|ref|NP_302424.1| pyruvate (or indolepyruvate) decarboxylase (*Mycobacterium leprae* TN); gi|118616174|ref|YP 904506.1| pyruvate or indole-3-pyruvate decarboxylase Pdc (*Mycobacterium ulcerans* Agy99); gi|67989660|ref|NP_001018185.1| hypothetical protein SPAC3H8.01 (*Schizosaccharomyces pombe* 972h–); gi|21666011|gb|AAM73540.1|AF282847_1 pyruvate decarboxylase PdcB (*Rhizopus oryzae*); gi|69291130|ref|ZP_00619161.1| Pyruvate decarboxylase: Pyruvate decarboxylase (*Kineococcus radiotolerans* SRS30216); gi|66363022|ref|XP_628477.1| pyruvate decarboxylase (*Cryptosporidium parvum* Iowa II); gi|70981398|ref|XP_731481.1| pyruvate decarboxylase (*Aspergillus fumigatus* Af293); gi|121704274|ref|XP_001270401.1| pyruvate decarboxylase, putative (*Aspergillus clavatus* NRRL 1); gi|119467089|ref|XP_001257351.1| pyruvate decarboxylase, putative (*Neosartorya fischeri* NRRL 181); gi|26554143|ref|NP_758077.1| pyruvate decarboxylase (*Mycoplasma penetrans* HF-2); gi|21666009|gb|AAM73539.1|AF282846_1 pyruvate decarboxylase PdcA (*Rhizopus oryzae*) each sequence associated with the accession numbers are incorporated herein by reference.

The 2-keto acid decarboxylase activity can be provided by one of the following genes: PDC6 from *Saccharomyces cerevisiae*, kivd from *Lactococcus lactis*, and THIS *Saccharomyces cerevisiae* (α-ketoisocaproate decarboxylase) and pdc *Clostridium acetobutylicum*. The alcohol dehydrogenase (Adh) activity can be provided by ADH2 from *Saccharomyces cerevisiae*.

In addition to the foregoing, the terms "2-ketoacid decarboxylase" or "kivD" refer to proteins that are capable of catalyzing the formation of pyruvate from phosphoenolpyruvate, and which share at least about 40%, 45%, 50%, 55%, 60%, 65%, 70%, 75%, 80%, 85%, 90%, 95%, 96%, 97%, 98%, 99% or greater sequence identity to SEQ ID NO:14, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes an alcohol dehydrogenase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes isobutanol from isobutanal. The alcohol dehydrogenase can be encoded by a Yahk gene, polynucleotide or homolog thereof. The Yahk gene or polynucleotide can be derived from various microorganisms including E. coli.

In addition to the foregoing, the terms "alcohol dehydrogenase" or "Yahk" refer to proteins that are capable of catalyzing the formation of pyruvate from phosphoenolpyruvate, and which share at least about 40%, 45%, 50%, 55%, 60%, 65%, 70%, 75%, 80%, 85%, 90%, 95%, 96%, 97%, 98%, 99% or greater sequence identity to SEQ ID NO:15, or at least about 50%, 60%, 70%, 80%, 90%, 95%, 96%, 97%, 98%, 99% or greater sequence similarity, as calculated by NCBI BLAST, using default parameters.

In all of the foregoing embodiments, a system or recombinant microorganism provided herein may include a purge valve. The purge valve includes an enzymatic reaction the vents/removes or otherwise eliminates over abundance of an excessive co-factor in order to maintain system function. For example, in one embodiment, the purge valve includes an NADH-oxidase (NoxE). The NADH oxidase can be encoded by a NoxE gene, polynucleotide or homolog thereof. The NoxE gene or polynucleotide can be derived from various microorganisms including L. lactis (see, e.g., Accession number YP_007507681).

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"), each of which is incorporated herein by reference in its entirety.

Examples of protocols sufficient to direct persons of skill through in vitro amplification methods, including the polymerase chain reaction (PCR), the ligase chain reaction (LCR), 0-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13:563-564.

Improved methods for cloning in vitro amplified nucleic acids are described in Wallace et al., U.S. Pat. No. 5,426,039.

Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The invention is illustrated in the following examples, which are provided by way of illustration and are not intended to be limiting.

EXAMPLES

Miller LB media or Miller LB-agar (BD Difco) was used for growth of bacterial strains in liquid or solid media. E. coli BL21Gold(DE3) [B, F–, ompT, hsdS$_B$, (r$_B$–,m$_B$–), dcm+, Tet$^r$, galλ, (DE3) endA Hte] (Agilent) was used as host for both cloning and expression of recombinant proteins using pET vectors. E. coli TOP10(DE3) [F– mcrA Δ(mrr-hsdRMS-mcrBC) Ψ801 acZΔM15 ΔlacX74 nupG recA1 araD139 Δ(ara-leu)7697 galE15 galK16 rpsL(Str$^R$) endA1 λ$^-$] was used for expression of recombinant proteins from the pBAD/p15A vector. Plasmids pET28a(+) and pET22b(+) were purchased from Novagen. HotStart Taq Mastermix (Denville) was used for gene amplification from genomic or plasmid DNA. Phusion DNA polymerase (Finnizymes), Taq DNA ligase (MCLab), and T5 Exonuclease (Epicenter) were purchased separately and used to make the assembly master mix (AMM) used for cloning. ATP, pyruvate, and NAD(P)' were from Sigma.

Plasmid Construction.

The expression plasmids for the enzymes were constructed from the pET28a plasmid backbone using the Nde1 and Sac1 cut sites to produce constructs with an N-terminal 6×His tag for purification. E. coli BL21-Gold cells were used as the host strain for enzyme expression. All enzymes were expressed in Luria-Bertani (LB) media supplemented with 50 μg/mL kanamycin and were induced with 0.2 mM isopropyl-β-D-1-thioglactopyranoside added to the culture at the end of log phase growth.

Enzyme Purification.

Cells from 0.5 L of culture were harvested by centrifugation and resuspended in 150 mM Tris pH 7.5, 100 mM NaCl. The cells were lysed on ice with sonication and the cell debris was removed by 12,000×g centrifugation at 4° C. The supernatant was then mixed with 5 mL nickel-nitrilotriacetic acid (NTA) agarose and after 30 minutes, the agarose slurry was loaded onto a gravity column and washed with five column volumes of 100 mM Tris pH 7.5, 100 mM NaCl, 15 mM imidazole. The enzyme was then eluted with 250 mM imidazole, 100 mM Tris pH 7.5. The resulting enzyme was dialyzed into 50 mM Tris pH 7.5, 50 mM NaCl and stored at 4° C.

Enzyme activity and optimization. All of the enzymes used in this work were assayed. The enzymes were assayed in 50 mM tris buffer pH 7.5, 5 mM MgCl, and 5 mM KCl which mirrors the final reaction conditions. The activity of NAD(P)H producing or consuming reactions were monitored at 340 nm. The activity of ATP consuming enzymes were monitored using a coupled assay with Zwf and NADP$^+$ at 340 nm.

ATPase assays of the enzymes were tested with 5 mM PEP, 1 mM ATP, 1 ul PK/LDH, 0.25 mM NADH and 5 ul of the given enzyme. The ATPase activity was calculated by the decrease in NADH concentration at 340 nm.

Final Isobutanol Reaction Conditions and Analysis.

The optimized self-sustaining reaction for the biotransformation glucose to isobutanol composed of 50 mM Tris pH 7.5, 5 mM MgCl, 5 mM KCl, 2 mM NADP$^+$, 4 mM ATP, 1 mM glutathione, 0.25 mM TPP, 0.25 mM MnCl, 4 mM Pi, 0.5 mM 2,3 BPG, and 660 mM glucose in a final reaction volume of 200 μL. The reactions were initiated with the addition of glucose, which was left out of the initial mixture. All reactions were performed at room temperature.

To assay for isobutanol, the reactions were incubated and extracted with 0.3 mL hexanes. 1 ul of the hexane layer was applied to a 0.25 micron HP-Innowax column using a HP 5890 Series II gas chromatogram. The GC method used an injection temperature that was held at 50° C. for 5 minutes before it was increased to 275° C. over 35 minutes. The peak intensities were compared to an authentic standard to assess concentrations.

A Stoichiometric Isobutanol Pathway.

A pathway was designed and implemented to make isobutanol with stoichiometric recycling of high energy cofactors. The 2-keto-acid isobutanol build phase employs 2 pyruvate and 2 NADPH, but no ATP, whereas the canonical glycolysis pathway produces 2 pyruvate, 2 NADH and 2 ATP. Thus to make the cofactor use stoichiometric the pathway needed (1) generate 2 NADPH rather than NADH and (2) eliminate net ATP production. With these constraints in mind, the 14 enzyme pathway shown in FIGS. 1 and 6 was developed in which glyceraldehyde phosphate dehydrogenase (GAPDH) and phosphoglycerate kinase (PGK) are replaced with a non-phosphorylating glyceraldehyde phosphate dehydrogenase (GAPN). The use of GAPN eliminates the production of 2 ATP and generates NADPH rather than NADH. The overall pathway becomes stoichiometric with respect to the production and consumption of both ATP and NADPH and has an overall theoretical carbon yield of 41%.

Figure 2A:
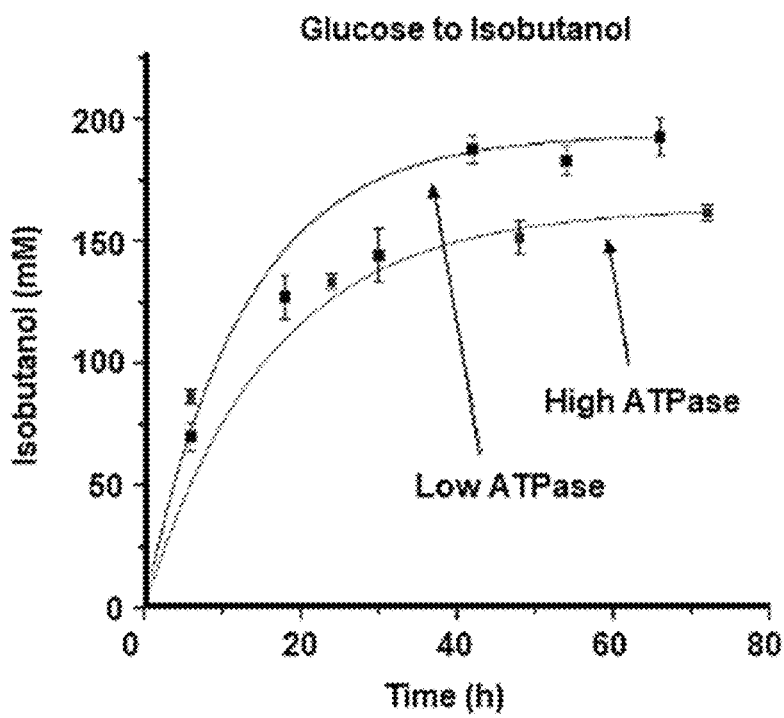
FIG. 2A-B shows results of the stoichiometric pathway from glucose to isobutanol. (A) Time course production from the stoichiometric pathway using a fully purified system. The initial time course production had a high amount of ATPase contamination and produced 11.96±1.57 g/L. The second time course had a lower amount of ATPase activity which increased the isobutanol production to 14.26±0.57 g/L. (B) Histogram of isobutanol production from the stoichiometric pathway after 48 hours after NADPH or ATP supplementation at 24 hours.

The overall pathway shown in FIG. 1 was first modeled using COPASI to identify likely key steps in the pathway. The model revealed that the relative activities of hexokinase and phosphofructokinase were useful for achieving flux through the system. The result makes sense because in glycolysis, hexokinase and phosphofructokinse compete with each other for any available ATP. Therefore, when the relative activity of hexokinase is too high, ATP can be rapidly exhausted in the production glucose-6-phosphate (G6P) leaving insufficient ATP for the phosphofructokinase reaction, ultimately stopping the carbon flux and killing the reaction. With this in mind, initial reactions were set up with hexokinase as the limiting enzyme. Once isobutanol production from glucose was detected, cofactor and enzyme concentrations were systematically optimized, resulting in the production time course seen in FIG. 2A. The high initial productivity sharply decreased by 18 hours rising to a titer of 161±3 mM isobutanol after 3 days (11.9±0.2 g/L).

As the pathway is stoichiometrically balanced with respect to ATP production and consumption, it was speculated that the sharp decrease in reaction rate might be due to ATPase activity in the system. Accordingly, ATPase activity was measure in each of the individual enzymes in the pathway and found that the enolase and ilvC enzyme preparations possessed notably higher ATPase levels than the other enzymes in the system. Accordingly, enolase and ilvC were repurified, which reduced contaminating ATPase activity. The stoichiometric reaction was set up again with the repurified enzymes, leading to an improved titer of 192±8 mM isobutanol over the course of three days (14.2±0.6 g/L). Nevertheless, production still decreased after 18 hours.

Figure 2B:
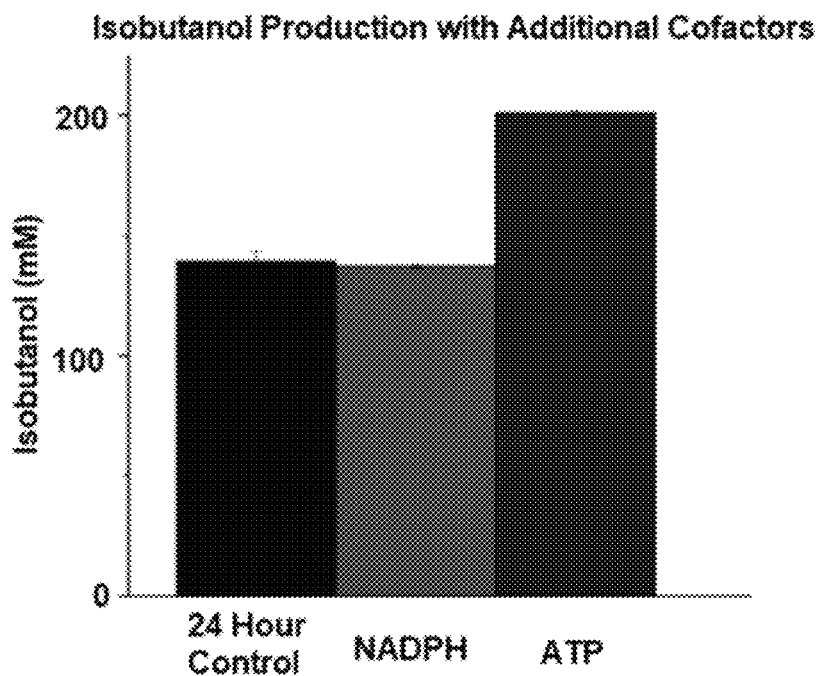

Test were performed to analyze if cofactor depletion remained a problem by initiating the reactions as usual and then adding another bolus of ATP or NADPH after 24 hours (FIG. 2B). After 48 hours, the reaction supplemented with NADPH showed no change in isobutanol production, but the ATP supplemented reaction increased isobutanol production by 41% over the control. These results suggest that ATP hydrolysis, whether by ATPase contamination or passive ATP hydrolysis, may be the limiting factor for isobutanol production in this stoichiometric pathway even after multiple attempts to purify away any ATPase contamination.

Design of an ATP Rheostat.

The results so far suggest that ATP depletion is a major problem for the long term sustainability of the stoichiometric reaction system. One way to deal with this problem might be to scrupulously purify all enzymes to eliminate any ATPase activity. But it may never be possible to completely eliminate spontaneous hydrolysis or hydrolysis by imperfect kinase reactions. Moreover, requiring completely pristine enzyme preparations is impractical on a large scale. Thus, a method to restore ATP levels as an intrinsic feature of the system was developed. To this end, a molecular rheostat was used.

The molecular rheostat (FIG. 3A) is made up two competing pathway branches that eventually transform glyceraldehyde-3 phosphate (G3P) into 3-phosphoglycerate (3PG). One branch generates ATP, while flow through the ATP generating branch is regulated by Pi levels. The first branch is made up of one enzyme, the non-phosphorylating GapN used in the stoichiometric pathway, which reduces $NADP^+$ to NADPH and converts G3P directly into 3PG without generating ATP. The second pathway is composed of two enzymes, an NADPH specific, phosphorylating glyceraldehyde-3-phosphate dehydrogenase (GapDH) and phosphoglycerate kinase (PGK), that also produces NADPH but first converts G3P into 1,3-bisphosphoglycerate (1,3BPG) followed by 3PG and ATP by the action of PGK. Therefore, the GapDH/PGK branch produces an additional ATP compared to the GapN only branch.

The relative flow through the ATP generating branch of the rheostat is controlled by free Pi, which acts as a proxy for the amount of ATP hydrolyzed to ADP and Pi. The function of the rheostat is easiest to see in the simplest case, where no exogenous Pi is added to the reaction (FIG. 3A). In this case there is initially no free Pi and there can be no flux through the phosphorylating GAPDH. Thus, in the absence of Pi, all the flux passes through GapN branch. Only when ATP is hydrolyzed to ADP and Pi, can the phosphorylating branch be utilized. Thus, the rheostat senses the depletion of ATP and acts to restore ATP by utilizing the phosphorylating GAPDH branch.

To explore the effectiveness of this design, a computer model of the overall pathway was made with and without the molecular rheostat system using COPASI (FIG. 4). As expected, the stoichiometric pathway, relying on GapN only, gradually winds down when any amount of ATP hydrolysis is introduced, much like what was observed experimentally. When this pathway is augmented with GapDH and PGK to complete the molecular rheostat, the reaction reaches a steady state and proceeds to completion. In this model the molecular rheostat reaches a steady state any time the flux through GapDH and PGK is greater than the ATPase activity that is modeled. This autoregulatory function means that the node will operate at a wide range of ATPase activities and that there is no need to perfectly tune and match the system to the specific amount of ATP hydrolysis for the system to reach a steady state. This autoregulatory behavior for ATP production is a key feature for designing easy to use, self-sustaining in vitro enzymatic pathways. In addition, modeling this pathway computationally allowed quick tests of the rheostat concept under an array of conditions and determine that increasing $P_i$, ATP, and hexokinase should result in an increase in the overall reaction rate.

Engineering Gap M6.

To implement the "molecular rheostat" module, GapDH enzyme was engineered that efficiently uses $NADP^+$. Both the *E. coli* GapDH (EcGap) and *G. stearothermophilus* GapDH (GsGap) prefer NAD' over NADP+ although the GsGap displays a higher basal activity with NADP+ than EcGap (which is absolutely specific for NAD+). Although the cofactor specificity of GsGap has adjusted before by sequence-based design, the mutant only slightly preferred NADP+ over NAD+. To more strongly flip the cofactor specificity of GsGap the crystal structure was examined and basic residues introduced into the loop region proximate to the 2'OH of NAD' that may help stabilize binding of a 2' phosphate in NADP+. A series of mutations were made altering residues D34, L35, and T36 of SEQ ID NO:6. The kinetics and specificity of the best enzyme, a D34A/L35R/T36K triple mutant (herein referred to as mGap), were obtained. The wild type GsGap enzyme has only modest activity with NADP+, but the triple mutant mGAP showed much improved activity with NADP at the expense of NAD'.

| Emyme | Cofactor | kcat (µM/min/mg) | KM (mM) | $k_{cat}/K_m$ |
|---|---|---|---|---|
| gapDH WT | NAD+ | 21.8 ± 2.6 | 1.5 ± 0.3 | 14.5 |
| | NADP+ | 1.2 ± 0.1 | 1.5 ± 0.5 | 2.1 |
| mGapDH | NAD+ | 0.2 ± 0.04 | 0.6 ± 0.4 | 0.4 |
| | NADP+ | 3.2 ± 0.1 | 0.3 ± 0.04 | 11.9 |

Isobutanol Production with Molecular Rheostat.

Figure 5A:
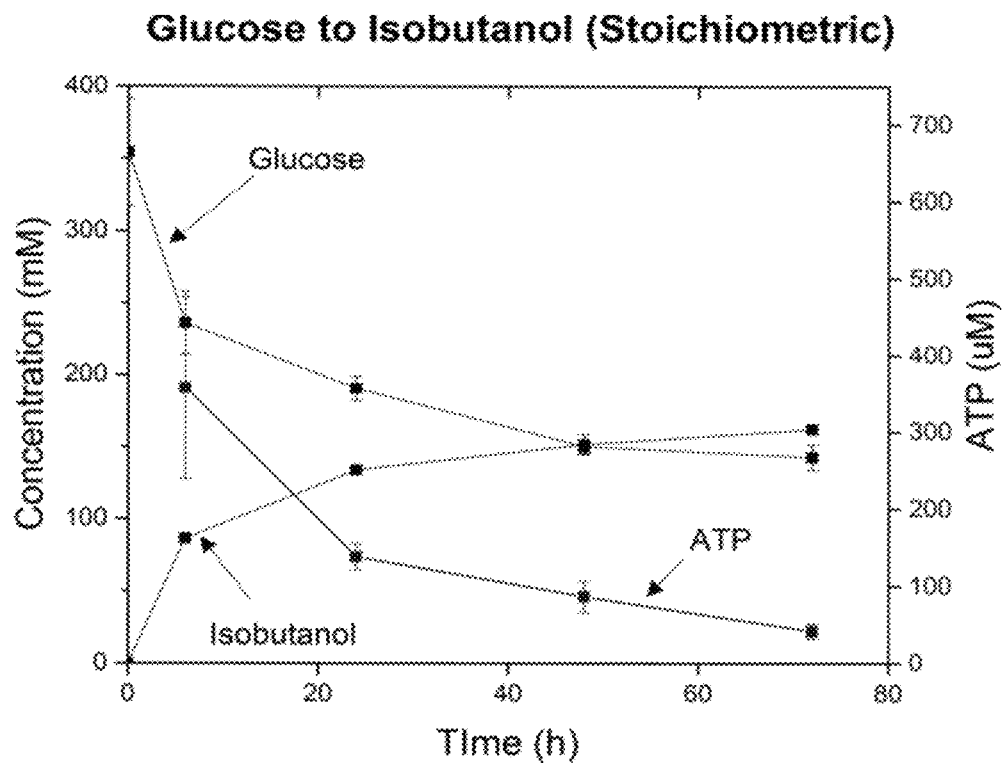
FIG. 5A-C shows the final production of isobutanol. (A) Shows a time course of the isobutanol production, glucose consumption, and ATP in the system using a stoichiometric pathway. (B) Shows a time course of the isobutanol production, glucose consumption and ATP in the ATP rheostat reaction. This reaction created a stead state of ATP at 600 uM and produced 2× as much isobutanol as the stoichiometric pathway. (C) Is a 24 hour histogram of isobutanol production from the stoichiometric system (gapN only), too much ATP production system (gapDH M6 only), and the rheostat system (both gapN and GapDH M6).
Figure 5B:
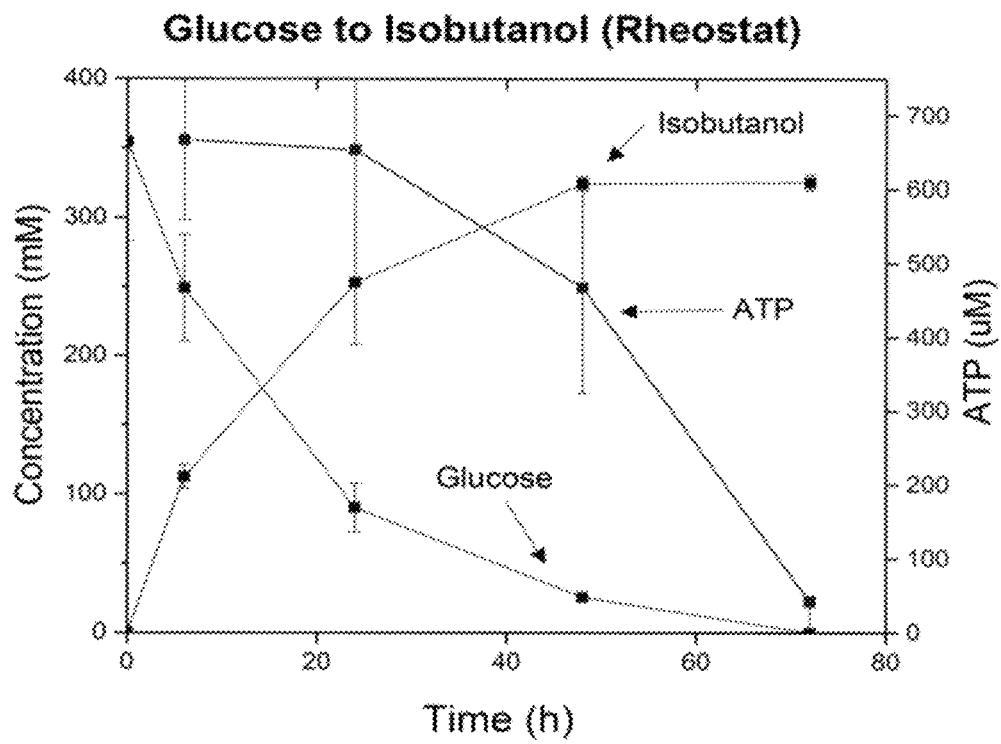

To implement the molecular rheostat for the production of isobutanol from glucose, the two enzymes mGap and PGK were added to the optimized stoichiometric reaction. To ensure sufficient ATP production through the molecular rheostat, the units of mGap and PGK activity in the reaction were an order of magnitude greater than the aggregate ATPase activity in the reaction. Reactions with and without the molecular rheostat were set up side-by-side over a 72 hour time course and were tested for Isobutanol production, residual glucose and ATP (FIG. 5A-B). The reaction with the molecular rheostat produced 24.1±1.8 g/L of isobutanol at 91.5% of the theoretical yield with a maximum productivity of 1.4±0.3 g/L/h. This isobutanol production represents a 101.7% improvement over the stoichiometric in vitro reaction and is higher than any published in vivo isobutanol production without the aid of complex in situ isobutanol removal.

The enzymes and enzyme concentrations in the final preparation pathway (see, e.g., FIG. 6A-B) are presented in the following table:

| Enzyme | Stock concentration (mg/mL) | Enzyme Activity (uM/min/mg) | Units/mL added to reaction |
|---|---|---|---|
| Sc Hk | 2.73 | 7.2 ± 0.1 | 0.025 |
| Gt PgiA | 5.7 | 19.2 ± 0.2 | 1.04 |
| Gs PfkA | 8.49 | 9.6 ± 0.2 | 3.260 |
| Sa FBA | 9.84 | 21.1 ± 0.3 | 8.305 |
| Gs TPI | 12.75 | 96.6 ± 5.4 | 12.317 |
| Sm GapN | 16.09 | 20.6 ± 2.7 | 9.944 |
| Gs Gsp M6 | 4.47 | 7.9 ± 0.4 | 0.177 |
| Gs PGK | 6.28 | 102.3 ± 2.9 | 3.212 |
| Gs PGM | 12.16 | 97.2 ± 13.0 | 17.729 |
| Ec Enolase | 26.09 | 82.5 ± 0.1 | 53.435 |
| Ec Pykf | 16.39 | 365.3 ± 37.9 | 299.363 |
| Bs AlsS | 6.22 | 6.94 ± 1.22 | 1.727 |
| Ec IlvC | 21.43 | 0.88 ± 0.23 | 1.509 |
| Re IlvD | 11.58 | 3.4 ± 0.3[1] | 1.575 |
| Ll KivD | 6.27 | 13.39 ± 2.28 | 0.672 |
| Ec Yahk | 2.18 | 3.64 ± 0.37 | 0.635 |

Figure 5C:
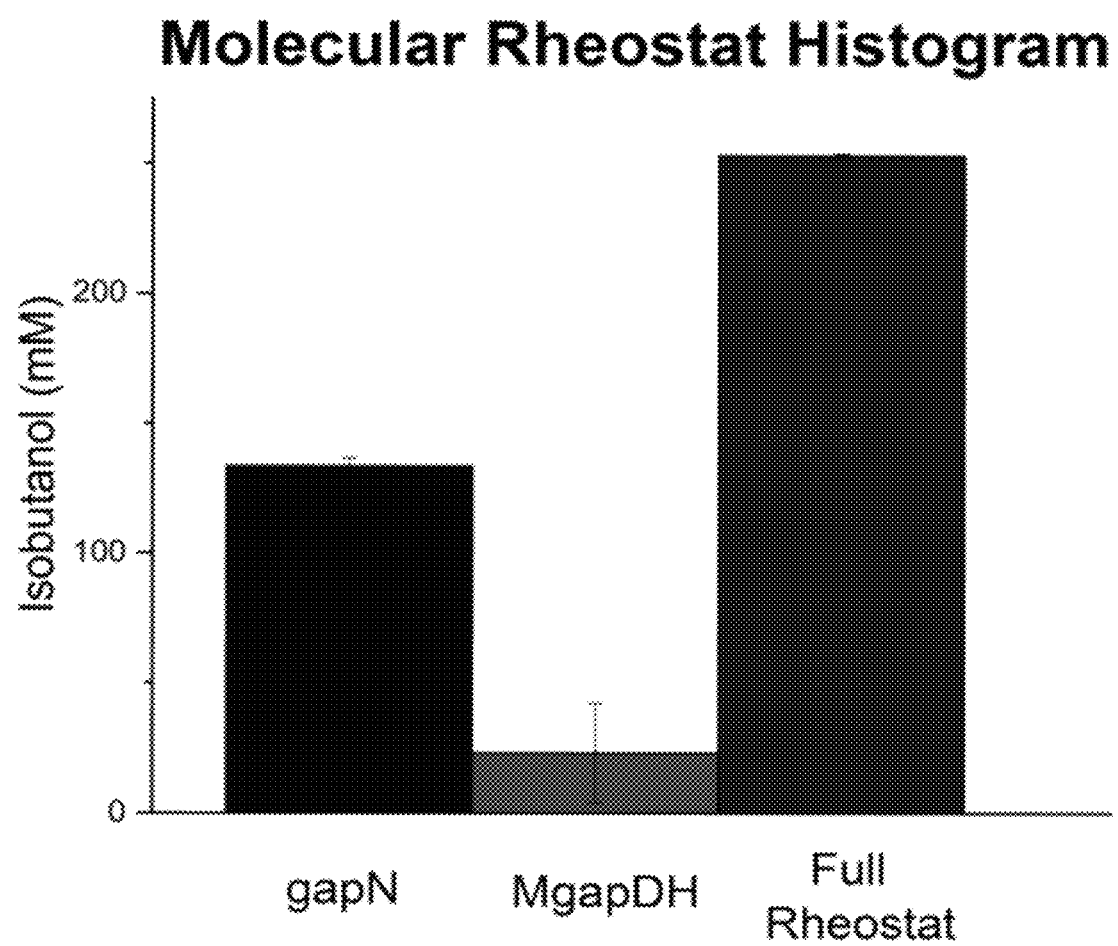
Figure 7:
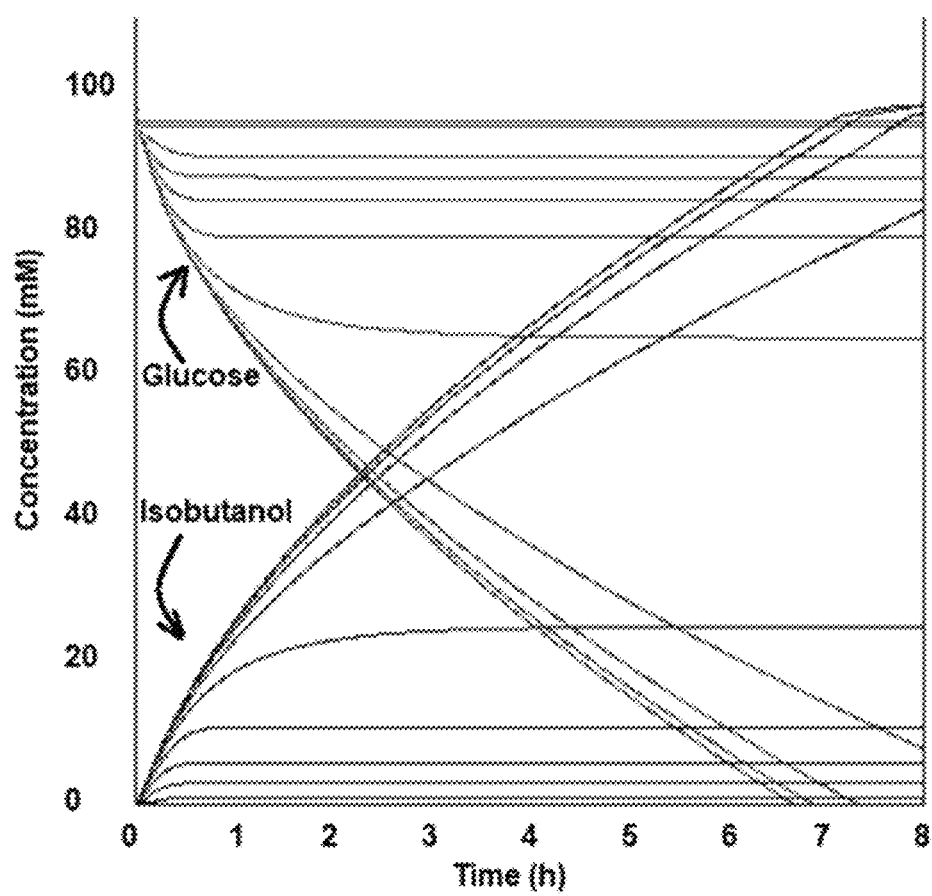
FIG. 7 provides a Caposi Model for hexokinase and the tope of glycolysis in the stoichiometric system.

The molecular rheostat performed as expected and maintain a higher ATP concentration relative to the stoichiometricly balanced reaction. The rheostat reaction held a steady state concentration of ATP of around 600 µM over 48 hours before the reaction stopped and the ATP concentration dropped. In contrast, the ATP concentration in the stoichiometric reaction steadily dropped throughout the entire run. Over the first 48 hours of both reactions there is a good correlation between the concentration of ATP in the reaction and the isobutanol productivity. Additionally, each component of the rheostat system was tested by leaving them out of the reaction and measuring the isobutanol produced after 24 hours (FIG. 5C). When either the GapN or mGap/PGK was left out, production of isobutanol was drastically reduced compared to the full molecular rheostat system.

Although the system containing the molecular rheostat produced a self-sustaining reaction and maintained a steady state of ATP for the first 48 hours, the reaction stopped at the 72 hour time point. In the reaction with the molecular rheostat, a precipitate was noticed that began to form after 24 hours which coincided with a decrease in isobutanol production. Upon completion of the reaction the precipitate was collected by centrifugation and separated by SDS-PAGE to identify proteins in the precipitate. Hexokinase was identified as the major constituent of the precipitate followed by KivD, and mGap. These results suggested that some of the enzymes were denaturing over time, possibly due to increasing isobutanol concentrations.

To determine the stability of each system component to isobutanol, each enzyme and cofactor in the pathway was tested for stability in 0%, 4% and 8% (saturating) isobtuanol. Hexokinase, GapN, mGap, and IlvC were most susceptible to isobutanol inactivation while most other enzymes and cofactors maintained significant activity at saturating levels of Isobutanol over 30 hours. These results rapidly identify a handful of priority enzymes that could be targeted for stability improvements to improve the overall sustainability of the system.

A number of embodiments of the invention have been described. Nevertheless, it will be understood that various modifications may be made without departing from the spirit and scope of the invention. Accordingly, other embodiments are within the scope of the following claims.

What is claimed is:

1. A recombinant, artificial or engineered metabolic pathway comprising a plurality of enzymatic steps that converts a substrate to a product, wherein the metabolic pathway comprises:
  a non-naturally occurring molecular rheostat system in which two distinct cofactor-dependent enzymatic pathways convert a first metabolite in the metabolic pathway to a downstream second metabolite within the metabolic pathway and wherein the distinct cofactor dependent enzymatic pathways produce different intermediate metabolites using a first distinct cofactor,
  wherein the first distinct enzymatic pathway provides an enzyme that directly converts the first metabolite to the downstream second metabolite, and
  wherein the second distinct enzymatic pathway provides a plurality of enzymes that converts the first metabolite to the downstream second metabolite,
  wherein the molecular rheostat alternates between or simultaneously uses the two distinct cofactor-dependent enzymatic pathways for the production of the downstream second metabolite depending upon the availability of a second distinct cofactor.

2. A recombinant, artificial or engineered metabolic pathway of claim 1, wherein the first distinct enzymatic pathway is active when the co-factor utilized by the second distinct enzymatic pathway level is low and wherein the second distinct enzymatic pathway is active when this co-factor level is high.

3. The recombinant, artificial or engineered pathway of claim 1, wherein the first cofactor utilized by the first distinct enzymatic pathway is an oxidizing/reducing co-factors and the second distinct enzymatic pathway cofactor is Pi.

4. The recombinant, artificial or engineered pathway of claim 3, wherein the oxidizing/reducing co-factors are $NAD^+/NADH$, $NADP^+/NADPH$ or $FAD^+/FADH$.

5. The recombinant, artificial or engineered pathway of claim 4, wherein the cofactor comprises $NADP^+/NADPH$.

6. The recombinant, artificial or engineered metabolic pathway of claim 1, wherein the metabolic pathway comprises the conversion of glyceraldehyde-3-phosphate to 3-phosphoglycerate.

7. The recombinant, artificial or engineered metabolic pathway of claim 6, wherein the metabolic pathway produces a product selected from the group consisting of isobutanol, 3-methyl-1-butanol, leucine, and valine.

8. The recombinant, artificial or engineered metabolic pathway of claim 6, wherein the second distinct enzymatic pathway comprises the conversion of glyceraldehyde-3-phosphate to 1,3-bisphosphoglycerate and 1,3-bisphosphoglycerate to 3-phosphoglycerate.

9. The recombinant artificial or engineered metabolic pathway of claim 6, wherein:
  (i) the first distinct enzyme pathway converts glyceraldehyde-3-phosphate (G3P) and $NADP^+$ to 3-phosphoglycerate (3PG) and NADPH; and
  (ii) the second enzyme pathway converts glyceraldehyde-3-phosphate (G3P), NADP+, and free phosphate (Pi) to 1,3-bisphosphoglycerate (1,3BPG) and converts 1,3 bisphosphoglycerate (1,3BPG) and ADP to 3-phosphoglycerate and ATP.

10. The recombinant artificial or engineered metabolic pathway of claim 9, wherein the enzyme of (i) comprises a NADP-dependent glyceraldehyde-3-phosphate dehydrogenase (GapN).

11. The recombinant artificial or engineered metabolic pathway of claim 10, wherein the GapN is obtained from *Streptococcus mutans*.

12. The recombinant artificial or engineered metabolic pathway of claim 9, wherein the enzyme of (ii) comprises a mutant glyceraldehyde-3-phosphate dehydrogenase (mGap) that comprises D34A/L35R/T36K mutations relative to SEQ ID NO: 6.

13. The recombinant artificial or engineered metabolic pathway of claim 9, wherein the enzyme of (ii) comprises a mutant glyceraldehyde-3-phosphate dehydrogenase (mGap) that has a sequence that shares is at least 95% sequence identity to SEQ ID NO: 6 and comprises D34A/L35R/T36K mutations.

14. The recombinant artificial or engineered metabolic pathway of claim 9, wherein an enzyme that converts 1,3 bisphosphoglycerate (1,3BPG) and ADP to 3-phosphoglycerate and ATP comprises an enzyme from enzyme commission number (EC number) EC 2.7.2.3.

15. The recombinant artificial or engineered metabolic pathway of claim 14, wherein the enzyme is a phosphoglycerate kinase.

16. The recombinant artificial or engineered metabolic pathway of claim 15, wherein the phosphoglycerate kinase is a Pgk from *Geobacillus stearothermophilus*.

17. The recombinant artificial or engineered metabolic pathway of claim 15, wherein the enzyme has a sequence that shares is at least 95% sequence identity to SEQ ID NO: 7 and has phosphoglycerate kinase activity.

18. The recombinant artificial or engineered metabolic pathway of claim 9, wherein the molecular rheostat comprise the enzymes of (i) a NADP-dependent glyceraldehyde-3-phosphate dehydrogenase (GapN), (ii) a mutant glyceraldehyde-3-phosphate dehydrogenase that utilizes $NADP^+$ and (iii) a phosphoglycerate kinase.

19. The recombinant artificial or engineered metabolic pathway of claim 1, wherein the pathway comprises:
  (i) an enzyme that catalyzes the production of glucose-6-phosphate (G6P) from glucose;
  (ii)) an enzyme that catalyzes the production of Fructose-6-phosphate (FGP) from glucose-6-phosphate (G6P);
  (iii)) an enzyme that catalyzes the conversion/phosphorylation of fructose-6-phosphate (F6P) to fructose-1,6-phosphate;
  (iv)) an enzyme that converts fructose-1,6-phosphate to two glyceraldehyde-3-phosphates (G3P);

(v) a molecular rheostat comprising:
  (a) an enzyme that converts glyceraldehyde-3-phosphate (G3P) and NADP+ to 3-phosphoglycerate (3PG) and NADPH and
  (b) an enzyme that converts glyceraldehyde-3-phosphate (G3P), NADP+ and free phosphate (Pi) to 1,3-bisphosphoglycerate (1,3BPG) and
  (c) an enzyme that converts 1,3 bisphosphglycerate (1,3BPG) and ADP to 3-phophoglycerate (3PG) and ATP;
(vi) a polypeptide that converts 3-phosphoglycerate (3PG) to 2-phosphoglycerate (2PG);
(vii)) an enzyme that converts 2-phosphoglycerate (2PG) to phosphoenolpyruvate (PEP);
(vii)) an enzyme that converts phosphoenolpyruvate (PEP) to pyruvate;
(ix)) an enzyme that converts pyruvate to acetolactate; (x) a polypeptide that converts acetolactate and NADPH to 2,3 dihydroxy-3-methyl butanoate and $NADP^+$;
(xi) a polypeptide that converts 2,3 dihydroxy-3-methyl butanoate to 3-methyl-2-oxobutanoate;
(xii)) an enzyme that converts 3-methyl-2-oxobutanoate to isobutanal; and
(xiii) a polypeptide that coverts isobutanal and NADPH to isobutanol and $NADP^+$.

20. The recombinant, artificial or engineered pathway of claim 1, wherein the metabolic pathway is in a cell-free system.

21. A recombinant polypeptide comprising a sequence that shares at least 95% sequence identity to SEQ ID NO: 6 and comprises D34A/L35R/T36K mutations and has glyceraldehyde-3-phosphate dehydrogenase activity.

* * * * *

SEQUENCE LISTING

<160> NUMBER OF SEQ ID NOS: 15

<210> SEQ ID NO 1
<211> LENGTH: 319
<212> TYPE: PRT
<213> ORGANISM: Geobacillus stearothermophilus

<400> SEQUENCE: 1

```
Met Lys Arg Ile Gly Val Leu Thr Ser Gly Gly Asp Ser Pro Gly Met
1               5                   10                  15

Asn Ala Ala Ile Arg Ser Val Val Arg Lys Ala Ile Tyr His Gly Val
            20                  25                  30

Glu Val Tyr Gly Val Tyr His Gly Tyr Ala Gly Leu Ile Ala Gly Asn
        35                  40                  45

Ile Lys Lys Leu Glu Val Gly Asp Val Gly Asp Ile Ile His Arg Gly
    50                  55                  60

Gly Thr Ile Leu Tyr Thr Ala Arg Cys Pro Glu Phe Lys Thr Glu Glu
65                  70                  75                  80

Gly Gln Lys Lys Gly Ile Glu Gln Leu Lys Lys His Gly Ile Glu Gly
                85                  90                  95

Leu Val Val Ile Gly Gly Asp Gly Ser Tyr Gln Gly Ala Lys Lys Leu
            100                 105                 110

Thr Glu His Gly Phe Pro Cys Val Gly Val Pro Gly Thr Ile Asp Asn
        115                 120                 125

Asp Ile Pro Gly Thr Asp Phe Thr Ile Gly Phe Asp Thr Ala Leu Asn
    130                 135                 140

Thr Val Ile Asp Ala Ile Asp Lys Ile Arg Asp Thr Ala Thr Ser His
145                 150                 155                 160

Glu Arg Thr Tyr Val Ile Glu Val Met Gly Arg His Ala Gly Asp Ile
                165                 170                 175

Ala Leu Trp Ser Gly Leu Ala Gly Gly Ala Glu Thr Ile Leu Ile Pro
            180                 185                 190

Glu Ala Asp Tyr Asp Met Asn Asp Val Ile Ala Arg Leu Lys Arg Gly
        195                 200                 205

His Glu Arg Gly Lys Lys His Ser Ile Ile Ile Val Ala Glu Gly Val
    210                 215                 220

Gly Ser Gly Val Asp Phe Gly Arg Gln Ile Gln Glu Ala Thr Gly Phe
225                 230                 235                 240

Glu Thr Arg Val Thr Val Leu Gly His Val Gln Arg Gly Gly Ser Pro
                245                 250                 255

Thr Ala Phe Asp Arg Val Leu Ala Ser Arg Leu Gly Ala Arg Ala Val
            260                 265                 270

Glu Leu Leu Leu Glu Gly Lys Gly Gly Arg Cys Val Gly Ile Gln Asn
        275                 280                 285

Asn Gln Leu Val Asp His Asp Ile Ala Glu Ala Leu Ala Asn Lys His
    290                 295                 300

Thr Ile Asp Gln Arg Met Tyr Ala Leu Ser Lys Glu Leu Ser Ile
305                 310                 315
```

<210> SEQ ID NO 2
<211> LENGTH: 253
<212> TYPE: PRT
<213> ORGANISM: Geobacillus stearothermophilus

<400> SEQUENCE: 2

```
Met Arg Lys Pro Ile Ile Ala Gly Asn Trp Lys Met His Lys Thr Leu
1               5                   10                  15

Ala Glu Ala Val Gln Phe Val Glu Asp Val Lys Gly His Val Pro Pro
            20                  25                  30

Ala Asp Glu Val Asp Ser Val Val Cys Ala Pro Phe Leu Phe Leu Asp
        35                  40                  45
```

```
Arg Leu Val Gln Ala Ala Asp Gly Thr Asp Leu Lys Ile Gly Ala Gln
 50                  55                  60

Thr Met His Phe Ala Asp Gln Gly Ala Tyr Thr Gly Glu Val Ser Pro
 65                  70                  75                  80

Val Met Leu Lys Asp Leu Gly Val Thr Tyr Val Ile Leu Gly His Ser
                 85                  90                  95

Glu Arg Arg Gln Met Phe Ala Glu Thr Asp Glu Thr Val Asn Lys Lys
                100                 105                 110

Val Leu Ala Ala Phe Thr Arg Gly Leu Ile Pro Ile Ile Cys Cys Gly
            115                 120                 125

Glu Ser Leu Glu Glu Arg Glu Ala Gly Gln Thr Asn Ala Val Val Ala
130                 135                 140

Ser Gln Val Glu Lys Ala Leu Ala Gly Leu Thr Pro Glu Gln Val Lys
145                 150                 155                 160

Gln Ala Val Ile Ala Tyr Glu Pro Ile Trp Ala Ile Gly Thr Gly Lys
                165                 170                 175

Ser Ser Thr Pro Glu Asp Ala Asn Ser Val Cys Gly His Ile Arg Ser
                180                 185                 190

Val Val Ser Arg Leu Phe Gly Pro Glu Ala Ala Glu Ala Ile Arg Ile
            195                 200                 205

Gln Tyr Gly Gly Ser Val Lys Pro Asp Asn Ile Arg Asp Phe Leu Ala
210                 215                 220

Gln Gln Gln Ile Asp Gly Ala Leu Val Gly Gly Ala Ser Leu Glu Pro
225                 230                 235                 240

Ala Ser Phe Leu Gln Leu Val Glu Ala Gly Arg His Glu
                245                 250

<210> SEQ ID NO 3
<211> LENGTH: 299
<212> TYPE: PRT
<213> ORGANISM: Staphylococcus aureus

<400> SEQUENCE: 3

Met Glu Ser Met Asn Lys Glu Gln Leu Glu Lys Met Lys Asn Gly Lys
 1               5                  10                  15

Gly Phe Ile Ala Ala Leu Asp Gln Ser Gly Ser Thr Pro Lys Ala
                20                  25                  30

Leu Lys Glu Tyr Gly Val Asn Glu Asp Gln Tyr Ser Asn Glu Asp Glu
             35                  40                  45

Met Phe Gln Leu Val His Asp Met Arg Thr Arg Val Val Thr Ser Pro
 50                  55                  60

Ser Phe Ser Pro Asp Lys Ile Leu Gly Ala Ile Leu Phe Glu Gln Thr
 65                  70                  75                  80

Met Asp Arg Glu Val Glu Ser Lys Tyr Thr Ala Asp Tyr Leu Ala Asp
                 85                  90                  95

Lys Gly Val Val Pro Phe Leu Lys Val Asp Lys Gly Leu Ala Glu Glu
                100                 105                 110

Gln Asn Gly Val Gln Leu Met Lys Pro Ile Asp Asn Leu Asp Asn Leu
            115                 120                 125

Leu Asp Arg Ala Asn Glu Arg His Ile Phe Gly Thr Lys Met Arg Ser
130                 135                 140

Asn Ile Leu Glu Leu Asn Glu Gln Gly Ile Lys Asp Val Val Glu Gln
145                 150                 155                 160

Gln Phe Glu Val Ala Lys Gln Ile Ile Ala Lys Gly Leu Val Pro Ile
```

```
            165                 170                 175
Ile Glu Pro Glu Val Asn Ile Asn Ala Lys Asp Lys Ala Glu Ile Glu
            180                 185                 190
Lys Val Leu Lys Ala Glu Leu Lys Lys Gly Leu Asp Ser Leu Asn Ala
        195                 200                 205
Asp Gln Leu Val Met Leu Lys Leu Thr Ile Pro Thr Glu Pro Asn Leu
        210                 215                 220
Tyr Lys Glu Leu Ala Glu His Pro Asn Val Val Arg Val Val Leu
225                 230                 235                 240
Ser Gly Gly Tyr Ser Arg Glu Lys Ala Asn Glu Leu Leu Lys Asp Asn
                245                 250                 255
Ala Glu Leu Ile Ala Ser Phe Ser Arg Ala Leu Ala Ser Asp Leu Arg
                260                 265                 270
Ala Asp Gln Ser Lys Glu Phe Asp Lys Ala Leu Gly Asp Ala Val
            275                 280                 285
Glu Ser Ile Tyr Asp Ala Ser Val Asn Lys Asn
            290                 295

<210> SEQ ID NO 4
<211> LENGTH: 449
<212> TYPE: PRT
<213> ORGANISM: Geobacillus thermodenitrificans

<400> SEQUENCE: 4

Met Thr His Ile Arg Phe Asp Tyr Ser Lys Ala Leu Ala Phe Phe Gly
1               5                   10                  15
Glu His Glu Leu Thr Tyr Leu Arg Asp Ala Val Lys Val Ala His His
                20                  25                  30
Ser Leu His Glu Lys Thr Gly Val Gly Asn Asp Phe Leu Gly Trp Leu
            35                  40                  45
Asp Trp Pro Val Asn Tyr Asp Lys Glu Glu Phe Ala Arg Ile Lys Gln
        50                  55                  60
Ala Ala Lys Lys Ile Gln Ser Asp Ser Asp Val Leu Leu Val Ile Gly
65                  70                  75                  80
Ile Gly Gly Ser Tyr Leu Gly Ala Arg Ala Ala Ile Glu Met Leu His
                85                  90                  95
His Ser Phe Tyr Asn Ala Leu Pro Lys Glu Lys Arg Ser Thr Pro Gln
            100                 105                 110
Ile Ile Phe Val Gly Asn Asn Ile Ser Ser Thr Tyr Met Lys Asp Val
        115                 120                 125
Ile Asp Phe Leu Glu Gly Lys Asp Phe Ser Ile Asn Val Ile Ser Lys
    130                 135                 140
Ser Gly Thr Thr Thr Glu Pro Ala Ile Ala Phe Arg Ile Phe Arg Lys
145                 150                 155                 160
Leu Leu Glu Asp Lys Tyr Gly Lys Glu Ala Arg Arg Ile Tyr
                165                 170                 175
Ala Thr Thr Asp Arg Ala Arg Gly Ala Leu Arg Thr Leu Ala Asp Glu
            180                 185                 190
Glu Gly Tyr Glu Thr Phe Val Ile Pro Asp Asp Ile Gly Gly Arg Tyr
        195                 200                 205
Ser Val Leu Thr Ala Val Gly Leu Leu Pro Ile Ala Ala Ser Gly Ala
    210                 215                 220
Asp Ile Asp Ala Met Met Glu Gly Ala Ala Lys Ala Arg Glu Asp Phe
225                 230                 235                 240
```

```
Ser Arg Ser Glu Leu Glu Glu Asn Ala Ala Tyr Gln Tyr Ala Ala Ile
            245                 250                 255

Arg Asn Ile Leu Tyr Asn Lys Gly Lys Thr Ile Glu Leu Leu Val Asn
        260                 265                 270

Tyr Glu Pro Ala Leu His Tyr Phe Ala Glu Trp Trp Lys Gln Leu Phe
            275                 280                 285

Gly Glu Ser Glu Gly Lys Asp Gln Lys Gly Ile Tyr Pro Ala Ser Ala
        290                 295                 300

Asp Phe Ser Thr Asp Leu His Ser Leu Gly Gln Tyr Ile Gln Glu Gly
305                 310                 315                 320

Arg Arg Asp Leu Phe Glu Thr Val Leu Lys Leu Glu Glu Pro Arg His
                325                 330                 335

Glu Leu Val Ile Glu Ala Glu Glu Ser Asp Leu Asp Gly Leu Asn Tyr
            340                 345                 350

Leu Ala Gly Gln Thr Val Asp Phe Val Asn Thr Lys Ala Phe Glu Gly
        355                 360                 365

Thr Leu Leu Ala His Thr Asp Gly Gly Val Pro Asn Leu Val Val Thr
    370                 375                 380

Leu Pro Lys Leu Asp Glu Tyr Thr Phe Gly Tyr Leu Val Tyr Phe Phe
385                 390                 395                 400

Glu Lys Ala Cys Ala Met Ser Gly Tyr Leu Leu Gly Val Asn Pro Phe
                405                 410                 415

Asp Gln Pro Gly Val Glu Ala Tyr Lys Lys Asn Met Phe Ala Leu Leu
            420                 425                 430

Gly Lys Pro Gly Tyr Glu Glu Leu Lys Asp Glu Leu Glu Lys Arg Leu
        435                 440                 445

Lys

<210> SEQ ID NO 5
<211> LENGTH: 475
<212> TYPE: PRT
<213> ORGANISM: Streptococcus mutans

<400> SEQUENCE: 5

Met Thr Lys Gln Tyr Lys Asn Tyr Val Asn Gly Glu Trp Lys Leu Ser
1               5                   10                  15

Glu Asn Glu Ile Lys Ile Tyr Glu Pro Ala Ser Gly Ala Glu Leu Gly
            20                  25                  30

Ser Val Pro Ala Met Ser Thr Glu Glu Val Asp Tyr Val Tyr Ala Ser
        35                  40                  45

Ala Lys Lys Ala Gln Pro Ala Trp Arg Ser Leu Ser Tyr Ile Glu Arg
    50                  55                  60

Ala Ala Tyr Leu His Lys Val Ala Asp Ile Leu Met Arg Asp Lys Glu
65                  70                  75                  80

Lys Ile Gly Ala Val Leu Ser Lys Glu Val Ala Lys Gly Tyr Lys Ser
                85                  90                  95

Ala Val Ser Glu Val Val Arg Thr Ala Glu Ile Ile Asn Tyr Ala Ala
            100                 105                 110

Glu Glu Gly Leu Arg Met Glu Gly Glu Val Leu Glu Gly Gly Ser Phe
        115                 120                 125

Glu Ala Ala Ser Lys Lys Lys Ile Ala Val Val Arg Arg Glu Pro Val
    130                 135                 140

Gly Leu Val Leu Ala Ile Ser Pro Phe Asn Tyr Pro Val Asn Leu Ala
145                 150                 155                 160
```

-continued

Gly Ser Lys Ile Ala Pro Ala Leu Ile Ala Gly Asn Val Ile Ala Phe
165 170 175

Lys Pro Pro Thr Gln Gly Ser Ile Ser Gly Leu Leu Ala Glu Ala
180 185 190

Phe Ala Glu Ala Gly Leu Pro Ala Gly Val Phe Asn Thr Ile Thr Gly
195 200 205

Arg Gly Ser Glu Ile Gly Asp Tyr Ile Val Glu His Gln Ala Val Asn
210 215 220

Phe Ile Asn Phe Thr Gly Ser Thr Gly Ile Gly Glu Arg Ile Gly Lys
225 230 235 240

Met Ala Gly Met Arg Pro Ile Met Leu Glu Leu Gly Gly Lys Asp Ser
245 250 255

Ala Ile Val Leu Glu Asp Ala Asp Leu Glu Leu Thr Ala Lys Asn Ile
260 265 270

Ile Ala Gly Ala Phe Gly Tyr Ser Gly Gln Arg Cys Thr Ala Val Lys
275 280 285

Arg Val Leu Val Met Glu Ser Val Ala Asp Glu Leu Val Glu Lys Ile
290 295 300

Arg Glu Lys Val Leu Ala Leu Thr Ile Gly Asn Pro Glu Asp Asp Ala
305 310 315 320

Asp Ile Thr Pro Leu Ile Asp Thr Lys Ser Ala Asp Tyr Val Glu Gly
325 330 335

Leu Ile Asn Asp Ala Asn Asp Lys Gly Ala Ala Leu Thr Glu Ile
340 345 350

Lys Arg Glu Gly Asn Leu Ile Cys Pro Ile Leu Phe Asp Lys Val Thr
355 360 365

Thr Asp Met Arg Leu Ala Trp Glu Glu Pro Phe Gly Pro Val Leu Pro
370 375 380

Ile Ile Arg Val Thr Ser Val Glu Glu Ala Ile Glu Ile Ser Asn Lys
385 390 395 400

Ser Glu Tyr Gly Leu Gln Ala Ser Ile Phe Thr Asn Asp Phe Pro Arg
405 410 415

Ala Phe Gly Ile Ala Glu Gln Leu Glu Val Gly Thr Val His Ile Asn
420 425 430

Asn Lys Thr Gln Arg Gly Thr Asp Asn Phe Pro Phe Leu Gly Ala Lys
435 440 445

Lys Ser Gly Ala Gly Ile Gln Gly Val Lys Tyr Ser Ile Glu Ala Met
450 455 460

Thr Thr Val Lys Ser Val Val Phe Asp Ile Lys
465 470 475

<210> SEQ ID NO 6
<211> LENGTH: 335
<212> TYPE: PRT
<213> ORGANISM: Geobacillus stearothermophilus

<400> SEQUENCE: 6

Met Ala Val Lys Val Gly Ile Asn Gly Phe Gly Arg Ile Gly Arg Asn
1 5 10 15

Val Phe Arg Ala Ala Leu Lys Asn Pro Asp Ile Glu Val Ala Val
20 25 30

Asn Asp Leu Thr Asp Ala Asn Thr Leu Ala His Leu Leu Lys Tyr Asp
35 40 45

Ser Val His Gly Arg Leu Asp Ala Glu Val Ser Val Asn Gly Asn Asn
50 55 60

```
Leu Val Val Asn Gly Lys Glu Ile Ile Val Lys Ala Glu Arg Asp Pro
 65                  70                  75                  80

Glu Asn Leu Ala Trp Gly Glu Ile Gly Val Asp Ile Val Val Glu Ser
                 85                  90                  95

Thr Gly Arg Phe Thr Lys Arg Glu Asp Ala Ala Lys His Leu Glu Ala
            100                 105                 110

Gly Ala Lys Lys Val Ile Ile Ser Ala Pro Ala Lys Asn Glu Asp Ile
        115                 120                 125

Thr Ile Val Met Gly Val Asn Gln Asp Lys Tyr Asp Pro Lys Ala His
130                 135                 140

His Val Ile Ser Asn Ala Ser Cys Thr Thr Asn Cys Leu Ala Pro Phe
145                 150                 155                 160

Ala Lys Val Leu His Glu Gln Phe Gly Ile Val Arg Gly Met Met Thr
                165                 170                 175

Thr Val His Ser Tyr Thr Asn Asp Gln Arg Ile Leu Asp Leu Pro His
            180                 185                 190

Lys Asp Leu Arg Arg Ala Arg Ala Ala Ala Glu Ser Ile Ile Pro Thr
        195                 200                 205

Thr Thr Gly Ala Ala Lys Ala Val Ala Leu Val Leu Pro Glu Leu Lys
210                 215                 220

Gly Lys Leu Asn Gly Met Ala Met Arg Val Pro Thr Pro Asn Val Ser
225                 230                 235                 240

Val Val Asp Leu Val Ala Glu Leu Glu Lys Glu Val Thr Val Glu Glu
                245                 250                 255

Val Asn Ala Ala Leu Lys Ala Ala Glu Gly Glu Leu Lys Gly Ile
            260                 265                 270

Leu Ala Tyr Ser Glu Glu Pro Leu Val Ser Arg Asp Tyr Asn Gly Ser
        275                 280                 285

Thr Val Ser Ser Thr Ile Asp Ala Leu Ser Thr Met Val Ile Asp Gly
290                 295                 300

Lys Met Val Lys Val Val Ser Trp Tyr Asp Asn Glu Thr Gly Tyr Ser
305                 310                 315                 320

His Arg Val Val Asp Leu Ala Ala Tyr Ile Ala Ser Lys Gly Leu
                325                 330                 335

<210> SEQ ID NO 7
<211> LENGTH: 394
<212> TYPE: PRT
<213> ORGANISM: Geobacillus stearothermophilus

<400> SEQUENCE: 7

Met Asn Lys Lys Thr Ile Arg Asp Val Asp Val Arg Gly Lys Arg Val
1               5                   10                  15

Phe Cys Arg Val Asp Phe Asn Val Pro Met Glu Gln Gly Ala Ile Thr
                20                  25                  30

Asp Asp Thr Arg Ile Arg Ala Ala Leu Pro Thr Ile Arg Tyr Leu Ile
            35                  40                  45

Glu His Gly Ala Lys Val Ile Leu Ala Ser His Leu Gly Arg Pro Lys
        50                  55                  60

Gly Lys Val Val Glu Glu Leu Arg Leu Asp Ala Val Ala Lys Arg Leu
65                  70                  75                  80

Gly Glu Leu Leu Glu Arg Pro Val Ala Lys Thr Asn Glu Ala Val Gly
                85                  90                  95

Asp Glu Val Lys Ala Ala Val Asp Arg Leu Asn Glu Gly Asp Val Leu
```

```
                100                 105                 110
Leu Leu Glu Asn Val Arg Phe Tyr Pro Gly Glu Glu Lys Asn Asp Pro
            115                 120                 125

Glu Leu Ala Lys Ala Phe Ala Glu Leu Ala Asp Leu Tyr Val Asn Asp
        130                 135                 140

Ala Phe Gly Ala Ala His Arg Ala His Ala Ser Thr Glu Gly Ile Ala
145                 150                 155                 160

His Tyr Leu Pro Ala Val Ala Gly Phe Leu Met Glu Lys Glu Leu Glu
                165                 170                 175

Val Leu Gly Lys Ala Leu Ser Asn Pro Asp Arg Pro Phe Thr Ala Ile
            180                 185                 190

Ile Gly Gly Ala Lys Val Lys Asp Lys Ile Gly Val Ile Asp Asn Leu
        195                 200                 205

Leu Glu Lys Val Asp Asn Leu Ile Ile Gly Gly Leu Ala Tyr Thr
    210                 215                 220

Phe Val Lys Ala Leu Gly His Asp Val Gly Lys Ser Leu Leu Glu Glu
225                 230                 235                 240

Asp Lys Ile Glu Leu Ala Lys Ser Phe Met Glu Lys Ala Lys Glu Lys
                245                 250                 255

Gly Val Arg Phe Tyr Met Pro Val Asp Val Val Ala Asp Arg Phe
            260                 265                 270

Ala Asn Asp Ala Asn Thr Lys Val Val Pro Ile Asp Ala Ile Pro Ala
        275                 280                 285

Asp Trp Ser Ala Leu Asp Ile Gly Pro Lys Thr Arg Glu Leu Tyr Arg
    290                 295                 300

Asp Val Ile Arg Glu Ser Lys Leu Val Val Trp Asn Gly Pro Met Gly
305                 310                 315                 320

Val Phe Glu Met Asp Ala Phe Ala His Gly Thr Lys Ala Ile Ala Glu
                325                 330                 335

Ala Leu Ala Glu Ala Leu Asp Thr Tyr Ser Val Ile Gly Gly Gly Asp
            340                 345                 350

Ser Ala Ala Ala Val Glu Lys Phe Gly Leu Ala Asp Lys Met Asp His
        355                 360                 365

Ile Ser Thr Gly Gly Gly Ala Ser Leu Glu Phe Met Glu Gly Lys Gln
    370                 375                 380

Leu Pro Gly Val Val Ala Leu Glu Asp Lys
385                 390

<210> SEQ ID NO 8
<211> LENGTH: 511
<212> TYPE: PRT
<213> ORGANISM: Geobacillus stearothermophilus

<400> SEQUENCE: 8

Met Ser Lys Lys Pro Val Ala Leu Ile Ile Leu Asp Gly Phe Ala Leu
1               5                   10                  15

Arg Asp Glu Thr Tyr Gly Asn Ala Val Ala Gln Ala Asn Lys Pro Asn
                20                  25                  30

Phe Asp Arg Tyr Trp Asn Glu Tyr Pro His Thr Thr Leu Lys Ala Cys
            35                  40                  45

Gly Glu Ala Val Gly Leu Pro Glu Gly Gln Met Gly Asn Ser Glu Val
        50                  55                  60

Gly His Leu Asn Ile Gly Ala Gly Arg Ile Val Tyr Gln Ser Leu Thr
65                  70                  75                  80
```

```
Arg Ile Asn Ile Ala Ile Arg Glu Gly Glu Phe Asp Arg Asn Glu Thr
                85                  90                  95

Phe Leu Ala Ala Met Asn His Val Lys Gln His Gly Thr Ser Leu His
            100                 105                 110

Leu Phe Gly Leu Leu Ser Asp Gly Gly Val His Ser Ile His His
        115                 120                 125

Leu Tyr Ala Leu Leu Arg Leu Ala Ala Lys Glu Gly Val Lys Arg Val
    130                 135                 140

Tyr Ile His Gly Phe Leu Asp Gly Arg Asp Val Gly Pro Gln Thr Ala
145                 150                 155                 160

Pro Gln Tyr Ile Lys Glu Leu Gln Glu Lys Ile Lys Glu Tyr Gly Val
                165                 170                 175

Gly Glu Ile Ala Thr Leu Ser Gly Arg Tyr Tyr Ser Met Asp Arg Asp
            180                 185                 190

Lys Arg Trp Asp Arg Val Glu Lys Ala Tyr Arg Ala Met Val Tyr Gly
        195                 200                 205

Glu Gly Pro Thr Tyr Arg Asp Pro Leu Glu Cys Ile Glu Asp Ser Tyr
    210                 215                 220

Lys His Gly Ile Tyr Asp Glu Phe Val Leu Pro Ser Val Ile Val Arg
225                 230                 235                 240

Glu Asp Gly Arg Pro Val Ala Thr Ile Gln Asp Asn Asp Ala Ile Ile
                245                 250                 255

Phe Tyr Asn Phe Arg Pro Asp Arg Ala Ile Gln Ile Ser Asn Thr Phe
            260                 265                 270

Thr Asn Glu Asp Phe Arg Glu Phe Asp Arg Gly Pro Lys His Pro Lys
        275                 280                 285

His Leu Phe Phe Val Cys Leu Thr His Phe Ser Glu Thr Val Lys Gly
    290                 295                 300

Tyr Val Ala Phe Lys Pro Thr Asn Leu Asp Asn Thr Ile Gly Glu Val
305                 310                 315                 320

Leu Ser Gln His Gly Leu Arg Gln Leu Arg Ile Ala Glu Thr Glu Lys
                325                 330                 335

Tyr Pro His Val Thr Phe Phe Met Ser Gly Gly Arg Glu Glu Lys Phe
            340                 345                 350

Pro Gly Glu Asp Arg Ile Leu Ile Asn Ser Pro Lys Val Pro Thr Tyr
        355                 360                 365

Asp Leu Lys Pro Glu Met Ser Ala Tyr Glu Val Thr Asp Ala Leu Leu
    370                 375                 380

Lys Glu Ile Glu Ala Asp Lys Tyr Asp Ala Ile Ile Leu Asn Tyr Ala
385                 390                 395                 400

Asn Pro Asp Met Val Gly His Ser Gly Lys Leu Glu Pro Thr Ile Lys
                405                 410                 415

Ala Val Glu Ala Val Asp Glu Cys Leu Gly Lys Val Val Asp Ala Ile
            420                 425                 430

Leu Ala Lys Gly Gly Ile Ala Ile Ile Thr Ala Asp His Gly Asn Ala
        435                 440                 445

Asp Glu Val Leu Thr Pro Asp Gly Lys Pro Gln Thr Ala His Thr Thr
    450                 455                 460

Asn Pro Val Pro Val Ile Val Thr Lys Lys Gly Ile Lys Leu Arg Asp
465                 470                 475                 480

Gly Gly Ile Leu Gly Asp Leu Ala Pro Thr Met Leu Asp Leu Leu Gly
                485                 490                 495

Leu Pro Gln Pro Lys Glu Met Thr Gly Lys Ser Leu Ile Val Lys
```

<210> SEQ ID NO 9
<211> LENGTH: 432
<212> TYPE: PRT
<213> ORGANISM: Escherichia coli

<400> SEQUENCE: 9

```
Met Ser Lys Ile Val Lys Ile Gly Arg Glu Ile Ile Asp Ser Arg
1               5                   10                  15

Gly Asn Pro Thr Val Glu Ala Glu Val His Leu Glu Gly Gly Phe Val
                20                  25                  30

Gly Met Ala Ala Ala Pro Ser Gly Ala Ser Thr Gly Ser Arg Glu Ala
            35                  40                  45

Leu Glu Leu Arg Asp Gly Asp Lys Ser Arg Phe Leu Gly Lys Gly Val
        50                  55                  60

Thr Lys Ala Val Ala Ala Val Asn Gly Pro Ile Ala Gln Ala Leu Ile
65                  70                  75                  80

Gly Lys Asp Ala Lys Asp Gln Ala Gly Ile Asp Lys Ile Met Ile Asp
                85                  90                  95

Leu Asp Gly Thr Glu Asn Lys Ser Lys Phe Gly Ala Asn Ala Ile Leu
            100                 105                 110

Ala Val Ser Leu Ala Asn Ala Lys Ala Ala Ala Ala Lys Gly Met
        115                 120                 125

Pro Leu Tyr Glu His Ile Ala Glu Leu Asn Gly Thr Pro Gly Lys Tyr
        130                 135                 140

Ser Met Pro Val Pro Met Met Asn Ile Ile Asn Gly Gly Glu His Ala
145                 150                 155                 160

Asp Asn Asn Val Asp Ile Gln Glu Phe Met Ile Gln Pro Val Gly Ala
                165                 170                 175

Lys Thr Val Lys Glu Ala Ile Arg Met Gly Ser Glu Val Phe His His
            180                 185                 190

Leu Ala Lys Val Leu Lys Ala Lys Gly Met Asn Thr Ala Val Gly Asp
        195                 200                 205

Glu Gly Gly Tyr Ala Pro Asn Leu Gly Ser Asn Ala Glu Ala Leu Ala
    210                 215                 220

Val Ile Ala Glu Ala Val Lys Ala Ala Gly Tyr Glu Leu Gly Lys Asp
225                 230                 235                 240

Ile Thr Leu Ala Met Asp Cys Ala Ala Ser Glu Phe Tyr Lys Asp Gly
                245                 250                 255

Lys Tyr Val Leu Ala Gly Glu Gly Asn Lys Ala Phe Thr Ser Glu Glu
            260                 265                 270

Phe Thr His Phe Leu Glu Glu Leu Thr Lys Gln Tyr Pro Ile Val Ser
        275                 280                 285

Ile Glu Asp Gly Leu Asp Glu Ser Asp Trp Asp Gly Phe Ala Tyr Gln
    290                 295                 300

Thr Lys Val Leu Gly Asp Lys Ile Gln Leu Val Gly Asp Asp Leu Phe
305                 310                 315                 320

Val Thr Asn Thr Lys Ile Leu Lys Glu Gly Ile Glu Lys Gly Ile Ala
                325                 330                 335

Asn Ser Ile Leu Ile Lys Phe Asn Gln Ile Gly Ser Leu Thr Glu Thr
            340                 345                 350

Leu Ala Ala Ile Lys Met Ala Lys Asp Ala Gly Tyr Thr Ala Val Ile
        355                 360                 365
```

Ser His Arg Ser Gly Glu Thr Glu Asp Ala Thr Ile Ala Asp Leu Ala
        370                 375                 380

Val Gly Thr Ala Ala Gly Gln Ile Lys Thr Gly Ser Met Ser Arg Ser
385                 390                 395                 400

Asp Arg Val Ala Lys Tyr Asn Gln Leu Ile Arg Ile Glu Glu Ala Leu
                405                 410                 415

Gly Glu Lys Ala Pro Tyr Asn Gly Arg Lys Glu Ile Lys Gly Gln Ala
            420                 425                 430

<210> SEQ ID NO 10
<211> LENGTH: 470
<212> TYPE: PRT
<213> ORGANISM: Escherichia coli

<400> SEQUENCE: 10

Met Lys Lys Thr Lys Ile Val Cys Thr Ile Gly Pro Lys Thr Glu Ser
1               5                   10                  15

Glu Glu Met Leu Ala Lys Met Leu Asp Ala Gly Met Asn Val Met Arg
            20                  25                  30

Leu Asn Phe Ser His Gly Asp Tyr Ala Glu His Gly Gln Arg Ile Gln
        35                  40                  45

Asn Leu Arg Asn Val Met Ser Lys Thr Gly Lys Thr Ala Ala Ile Leu
    50                  55                  60

Leu Asp Thr Lys Gly Pro Glu Ile Arg Thr Met Lys Leu Glu Gly Gly
65                  70                  75                  80

Asn Asp Val Ser Leu Lys Ala Gly Gln Thr Phe Thr Phe Thr Thr Asp
                85                  90                  95

Lys Ser Val Ile Gly Asn Ser Glu Met Val Ala Val Thr Tyr Glu Gly
            100                 105                 110

Phe Thr Thr Asp Leu Ser Val Gly Asn Thr Val Leu Val Asp Asp Gly
        115                 120                 125

Leu Ile Gly Met Glu Val Thr Ala Ile Glu Gly Asn Lys Val Ile Cys
    130                 135                 140

Lys Val Leu Asn Asn Gly Asp Leu Gly Glu Asn Lys Gly Val Asn Leu
145                 150                 155                 160

Pro Gly Val Ser Ile Ala Leu Pro Ala Leu Ala Glu Lys Asp Lys Gln
                165                 170                 175

Asp Leu Ile Phe Gly Cys Glu Gln Gly Val Asp Phe Val Ala Ala Ser
            180                 185                 190

Phe Ile Arg Lys Arg Ser Asp Val Ile Glu Ile Arg Glu His Leu Lys
        195                 200                 205

Ala His Gly Gly Glu Asn Ile His Ile Ile Ser Lys Ile Glu Asn Gln
    210                 215                 220

Glu Gly Leu Asn Asn Phe Asp Glu Ile Leu Glu Ala Ser Asp Gly Ile
225                 230                 235                 240

Met Val Ala Arg Gly Asp Leu Gly Val Glu Ile Pro Val Glu Glu Val
                245                 250                 255

Ile Phe Ala Gln Lys Met Met Ile Glu Lys Cys Ile Arg Ala Arg Lys
            260                 265                 270

Val Val Ile Thr Ala Thr Gln Met Leu Asp Ser Met Ile Lys Asn Pro
        275                 280                 285

Arg Pro Thr Arg Ala Glu Ala Gly Asp Val Ala Asn Ala Ile Leu Asp
    290                 295                 300

Gly Thr Asp Ala Val Met Leu Ser Gly Glu Ser Ala Lys Gly Lys Tyr
305                 310                 315                 320

```
Pro Leu Glu Ala Val Ser Ile Met Ala Thr Ile Cys Glu Arg Thr Asp
            325                 330                 335

Arg Val Met Asn Ser Arg Leu Glu Phe Asn Asn Asp Asn Arg Lys Leu
            340                 345                 350

Arg Ile Thr Glu Ala Val Cys Arg Gly Ala Val Glu Thr Ala Glu Lys
            355                 360                 365

Leu Asp Ala Pro Leu Ile Val Ala Thr Gln Gly Gly Lys Ser Ala
            370                 375             380

Arg Ala Val Arg Lys Tyr Phe Pro Asp Ala Thr Ile Leu Ala Leu Thr
385                 390                 395                 400

Thr Asn Glu Lys Thr Ala His Gln Leu Val Leu Ser Lys Gly Val Val
                405                 410                 415

Pro Gln Leu Val Lys Glu Ile Thr Ser Thr Asp Asp Phe Tyr Arg Leu
            420                 425                 430

Gly Lys Glu Leu Ala Leu Gln Ser Gly Leu Ala His Lys Gly Asp Val
            435                 440                 445

Val Val Met Val Ser Gly Ala Leu Val Pro Ser Gly Thr Thr Asn Thr
            450                 455                 460

Ala Ser Val His Val Leu
465                 470

<210> SEQ ID NO 11
<211> LENGTH: 571
<212> TYPE: PRT
<213> ORGANISM: Bacillus subtilis

<400> SEQUENCE: 11

Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
            35                  40                  45

Gln Asp Lys Gly Pro Glu Ile Ile Val Ala Arg His Glu Gln Asn Ala
        50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
            115                 120                 125

Ala Ala Leu Phe Gln Pro Ile Thr Lys Tyr Ser Val Glu Val Gln Asp
        130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
            195                 200                 205

Gln Thr Ala Lys Leu Pro Val Val Leu Val Gly Met Lys Gly Gly Arg
```

```
            210                 215                 220
Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
                340                 345                 350

Leu Ser Asp Leu Lys Gln Tyr Met His Glu Gly Glu Gln Val Pro Ala
            355                 360                 365

Asp Trp Lys Ser Asp Arg Ala His Pro Leu Glu Ile Val Lys Glu Leu
370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
            435                 440                 445

Ser Gly Asp Gly Gly Phe Leu Phe Ser Ala Met Glu Leu Glu Thr Ala
        450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
                500                 505                 510

Gly Ala Thr Gly Leu Arg Val Glu Ser Pro Asp Gln Leu Ala Asp Val
            515                 520                 525

Leu Arg Gln Gly Met Asn Ala Glu Gly Pro Val Ile Ile Asp Val Pro
        530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 12
<211> LENGTH: 491
<212> TYPE: PRT
<213> ORGANISM: Escherichia coli

<400> SEQUENCE: 12

Met Ala Asn Tyr Phe Asn Thr Leu Asn Leu Arg Gln Gln Leu Ala Gln
1               5                   10                  15
```

```
Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
                35                  40                  45

Gly Leu Asn Gln Gly Leu Asn Met Arg Asp Ser Gly Leu Asp Ile Ser
 50                  55                  60

Tyr Ala Leu Arg Lys Glu Ala Ile Ala Glu Lys Arg Ala Ser Trp Arg
 65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
            115                 120                 125

Gly Tyr Ser His Gly Phe Asn Ile Val Glu Val Gly Glu Gln Ile Arg
130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
            195                 200                 205

Ser Phe Val Ala Glu Val Lys Ser Asp Leu Met Gly Glu Gln Thr Ile
210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
            275                 280                 285

Ser Glu Gln Leu Lys Glu Ile Met Ala Pro Leu Phe Gln Lys His Met
290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
            355                 360                 365

Val Glu Leu Ala Phe Glu Thr Met Val Asp Ser Gly Ile Ile Glu Glu
            370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
```

```
                435                 440                 445
Pro Glu Gly Ala Val Asp Asn Gly Gln Leu Arg Asp Val Asn Glu Ala
    450                 455                 460
Ile Arg Ser His Ala Ile Glu Gln Val Gly Lys Lys Leu Arg Gly Tyr
465                 470                 475                 480
Met Thr Asp Met Lys Arg Ile Ala Val Ala Gly
                485                 490

<210> SEQ ID NO 13
<211> LENGTH: 616
<212> TYPE: PRT
<213> ORGANISM: Escherichia coli

<400> SEQUENCE: 13

Met Pro Lys Tyr Arg Ser Ala Thr Thr Thr His Gly Arg Asn Met Ala
1               5                   10                  15
Gly Ala Arg Ala Leu Trp Arg Ala Thr Gly Met Thr Asp Ala Asp Phe
                20                  25                  30
Gly Lys Pro Ile Ile Ala Val Val Asn Ser Phe Thr Gln Phe Val Pro
            35                  40                  45
Gly His Val His Leu Arg Asp Leu Gly Lys Leu Val Ala Glu Gln Ile
        50                  55                  60
Glu Ala Ala Gly Gly Val Ala Lys Glu Phe Asn Thr Ile Ala Val Asp
65                  70                  75                  80
Asp Gly Ile Ala Met Gly His Gly Gly Met Leu Tyr Ser Leu Pro Ser
                85                  90                  95
Arg Glu Leu Ile Ala Asp Ser Val Glu Tyr Met Val Asn Ala His Cys
            100                 105                 110
Ala Asp Ala Met Val Cys Ile Ser Asn Cys Asp Lys Ile Thr Pro Gly
        115                 120                 125
Met Leu Met Ala Ser Leu Arg Leu Asn Ile Pro Val Ile Phe Val Ser
130                 135                 140
Gly Gly Pro Met Glu Ala Gly Lys Thr Lys Leu Ser Asp Gln Ile Ile
145                 150                 155                 160
Lys Leu Asp Leu Val Asp Ala Met Ile Gln Gly Ala Asp Pro Lys Val
                165                 170                 175
Ser Asp Ser Gln Ser Asp Gln Val Glu Arg Ser Ala Cys Pro Thr Cys
            180                 185                 190
Gly Ser Cys Ser Gly Met Phe Thr Ala Asn Ser Met Asn Cys Leu Thr
        195                 200                 205
Glu Ala Leu Gly Leu Ser Gln Pro Gly Asn Gly Ser Leu Leu Ala Thr
    210                 215                 220
His Ala Asp Arg Lys Gln Leu Phe Leu Asn Ala Gly Lys Arg Ile Val
225                 230                 235                 240
Glu Leu Thr Lys Arg Tyr Tyr Glu Gln Asn Asp Glu Ser Ala Leu Pro
                245                 250                 255
Arg Asn Ile Ala Ser Lys Ala Ala Phe Glu Asn Ala Met Thr Leu Asp
            260                 265                 270
Ile Ala Met Gly Gly Ser Thr Asn Thr Val Leu His Leu Leu Ala Ala
        275                 280                 285
Ala Gln Glu Ala Glu Ile Asp Phe Thr Met Ser Asp Ile Asp Lys Leu
    290                 295                 300
Ser Arg Lys Val Pro Gln Leu Cys Lys Val Ala Pro Ser Thr Gln Lys
305                 310                 315                 320
```

```
Tyr His Met Glu Asp Val His Arg Ala Gly Val Ile Gly Ile Leu
            325                 330                 335

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
            355                 360                 365

Thr Gln Asp Asp Ala Val Lys Asn Met Phe Arg Ala Gly Pro Ala Gly
        370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
            435                 440                 445

Thr Gly Pro Ala Lys Val Tyr Glu Ser Gln Asp Ala Val Glu Ala
        450                 455                 460

Ile Leu Gly Gly Lys Val Val Ala Gly Asp Val Val Ile Arg Tyr
465                 470                 475                 480

Glu Gly Pro Lys Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510

Asp Gly Arg Phe Ser Gly Thr Ser Gly Leu Ser Ile Gly His Val
            515                 520                 525

Ser Pro Glu Ala Ala Ser Gly Gly Ser Ile Gly Leu Ile Glu Asp Gly
        530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
            595                 600                 605

Arg Asp Lys Ser Lys Leu Gly Gly
        610                 615

<210> SEQ ID NO 14
<211> LENGTH: 548
<212> TYPE: PRT
<213> ORGANISM: Lactococcus lactis

<400> SEQUENCE: 14

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80
```

```
Asn Gly Leu Ala Gly Ser Tyr Ala Glu Asn Leu Pro Val Val Glu Ile
                85                  90                  95
Val Gly Ser Pro Thr Ser Lys Val Gln Asn Glu Gly Lys Phe Val His
            100                 105                 110
His Thr Leu Ala Asp Gly Asp Phe Lys His Phe Met Lys Met His Glu
        115                 120                 125
Pro Val Thr Ala Ala Arg Thr Leu Leu Thr Ala Glu Asn Ala Thr Val
    130                 135                 140
Glu Ile Asp Arg Val Leu Ser Ala Leu Leu Lys Glu Arg Lys Pro Val
145                 150                 155                 160
Tyr Ile Asn Leu Pro Val Asp Val Ala Ala Lys Ala Glu Lys Pro
                165                 170                 175
Ser Leu Pro Leu Lys Lys Glu Asn Ser Thr Ser Asn Thr Ser Asp Gln
            180                 185                 190
Glu Ile Leu Asn Lys Ile Gln Glu Ser Leu Lys Asn Ala Lys Lys Pro
        195                 200                 205
Ile Val Ile Thr Gly His Glu Ile Ile Ser Phe Gly Leu Glu Lys Thr
    210                 215                 220
Val Ser Gln Phe Ile Ser Lys Thr Lys Leu Pro Ile Thr Thr Leu Asn
225                 230                 235                 240
Phe Gly Lys Ser Ser Val Asp Glu Ala Leu Pro Ser Phe Leu Gly Ile
                245                 250                 255
Tyr Asn Gly Lys Leu Ser Glu Pro Asn Leu Lys Glu Phe Val Glu Ser
            260                 265                 270
Ala Asp Phe Ile Leu Met Leu Gly Val Lys Leu Thr Asp Ser Ser Thr
        275                 280                 285
Gly Ala Phe Thr His His Leu Asn Glu Asn Lys Met Ile Ser Leu Asn
    290                 295                 300
Ile Asp Glu Gly Lys Ile Phe Asn Glu Ser Ile Gln Asn Phe Asp Phe
305                 310                 315                 320
Glu Ser Leu Ile Ser Ser Leu Asp Leu Ser Glu Ile Glu Tyr Lys
                325                 330                 335
Gly Lys Tyr Ile Asp Lys Lys Gln Glu Asp Phe Val Pro Ser Asn Ala
            340                 345                 350
Leu Leu Ser Gln Asp Arg Leu Trp Gln Ala Val Glu Asn Leu Thr Gln
        355                 360                 365
Ser Asn Glu Thr Ile Val Ala Glu Gln Gly Thr Ser Phe Phe Gly Ala
    370                 375                 380
Ser Ser Ile Phe Leu Lys Pro Lys Ser His Phe Ile Gly Gln Pro Leu
385                 390                 395                 400
Trp Gly Ser Ile Gly Tyr Thr Phe Pro Ala Ala Leu Gly Ser Gln Ile
                405                 410                 415
Ala Asp Lys Glu Ser Arg His Leu Leu Phe Ile Gly Asp Gly Ser Leu
            420                 425                 430
Gln Leu Thr Val Gln Glu Leu Gly Leu Ala Ile Arg Glu Lys Ile Asn
        435                 440                 445
Pro Ile Cys Phe Ile Ile Asn Asn Asp Gly Tyr Thr Val Glu Arg Glu
    450                 455                 460
Ile His Gly Pro Asn Gln Ser Tyr Asn Asp Ile Pro Met Trp Asn Tyr
465                 470                 475                 480
Ser Lys Leu Pro Glu Ser Phe Gly Ala Thr Glu Glu Arg Val Val Ser
                485                 490                 495
```

```
Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
            515                 520                 525

Glu Asp Ala Pro Lys Val Leu Lys Lys Met Gly Lys Leu Phe Ala Glu
530                 535                 540

Gln Asn Lys Ser
545

<210> SEQ ID NO 15
<211> LENGTH: 349
<212> TYPE: PRT
<213> ORGANISM: Escherichia coli

<400> SEQUENCE: 15

Met Lys Ile Lys Ala Val Gly Ala Tyr Ser Ala Lys Gln Pro Leu Glu
1               5                   10                  15

Pro Met Asp Ile Thr Arg Arg Glu Pro Gly Pro Asn Asp Val Lys Ile
            20                  25                  30

Glu Ile Ala Tyr Cys Gly Val Cys His Ser Asp Leu His Gln Val Arg
        35                  40                  45

Ser Glu Trp Ala Gly Thr Val Tyr Pro Cys Val Pro Gly His Glu Ile
    50                  55                  60

Val Gly Arg Val Val Ala Val Gly Asp Gln Val Glu Lys Tyr Ala Pro
65                  70                  75                  80

Gly Asp Leu Val Gly Val Gly Cys Ile Val Asp Ser Cys Lys His Cys
                85                  90                  95

Glu Glu Cys Glu Asp Gly Leu Glu Asn Tyr Cys Asp His Met Thr Gly
            100                 105                 110

Thr Tyr Asn Ser Pro Thr Pro Asp Glu Pro Gly His Thr Leu Gly Gly
        115                 120                 125

Tyr Ser Gln Gln Ile Val Val His Glu Arg Tyr Val Leu Arg Ile Arg
    130                 135                 140

His Pro Gln Glu Gln Leu Ala Ala Val Ala Pro Leu Leu Cys Ala Gly
145                 150                 155                 160

Ile Thr Thr Tyr Ser Pro Leu Arg His Trp Gln Ala Gly Pro Gly Lys
                165                 170                 175

Lys Val Gly Val Val Gly Ile Gly Gly Leu Gly His Met Gly Ile Lys
            180                 185                 190

Leu Ala His Ala Met Gly Ala His Val Val Ala Phe Thr Thr Ser Glu
        195                 200                 205

Ala Lys Arg Glu Ala Ala Lys Ala Leu Gly Ala Asp Glu Val Val Asn
    210                 215                 220

Ser Arg Asn Ala Asp Glu Met Ala Ala His Leu Lys Ser Phe Asp Phe
225                 230                 235                 240

Ile Leu Asn Thr Val Ala Ala Pro His Asn Leu Asp Asp Phe Thr Thr
                245                 250                 255

Leu Leu Lys Arg Asp Gly Thr Met Thr Leu Val Gly Ala Pro Ala Thr
            260                 265                 270

Pro His Lys Ser Pro Glu Val Phe Asn Leu Ile Met Lys Arg Arg Ala
        275                 280                 285

Ile Ala Gly Ser Met Ile Gly Gly Ile Pro Glu Thr Gln Glu Met Leu
    290                 295                 300

Asp Phe Cys Ala Glu His Gly Ile Val Ala Asp Ile Glu Met Ile Arg
305                 310                 315                 320
```

```
Ala Asp Gln Ile Asn Glu Ala Tyr Glu Arg Met Leu Arg Gly Asp Val
            325                 330                 335

Lys Tyr Arg Phe Val Ile Asp Asn Arg Thr Leu Thr Asp
            340                 345
```